(12) United States Patent
Martin et al.

(10) Patent No.: US 8,348,939 B2
(45) Date of Patent: Jan. 8, 2013

(54) ABLATION DEVICE WITH SENSOR

(75) Inventors: Keith Edward Martin, Mason, OH (US); Salvatore Privitera, Mason, OH (US); Christopher J. Park, Oregonia, OH (US)

(73) Assignee: AtriCure, Inc., West Chester, OH (US)

( * ) Notice: Subject to any disclaimer, the term of this patent is extended or adjusted under 35 U.S.C. 154(b) by 0 days.

(21) Appl. No.: 13/221,503

(22) Filed: Aug. 30, 2011

(65) Prior Publication Data

US 2011/0313413 A1 Dec. 22, 2011

Related U.S. Application Data

(60) Division of application No. 11/457,919, filed on Jul. 17, 2006, now Pat. No. 8,034,051, which is a continuation-in-part of application No. 11/363,707, filed on Feb. 28, 2006, now Pat. No. 7,828,795.

(60) Provisional application No. 60/699,679, filed on Jul. 15, 2005.

(51) Int. Cl.
*A61B 18/14* (2006.01)
(52) U.S. Cl. .......................... 606/41; 606/50
(58) Field of Classification Search .............. 606/41, 606/45–52
See application file for complete search history.

(56) References Cited

U.S. PATENT DOCUMENTS

| | | | |
|---|---|---|---|
| 1,916,722 A * | 7/1933 | Ende ........................... | 606/50 |
| 4,026,303 A | 5/1977 | Babotai | |
| 4,074,718 A | 2/1978 | Morrison, Jr. | |
| 5,197,964 A * | 3/1993 | Parins ........................... | 606/48 |
| 5,230,349 A | 7/1993 | Langberg | |
| 5,341,807 A | 8/1994 | Nardella | |
| 5,398,683 A | 3/1995 | Edwards et al. | |
| 5,558,671 A | 9/1996 | Yates | |
| 5,634,924 A | 6/1997 | Turkel et al. | |
| 5,688,267 A | 11/1997 | Panescu et al. | |
| 5,846,241 A * | 12/1998 | Kittur et al. ................... | 606/48 |
| 5,916,213 A | 6/1999 | Haissaguerre et al. | |
| 5,967,976 A | 10/1999 | Larsen et al. | |

(Continued)

FOREIGN PATENT DOCUMENTS

WO    WO 2004/103195    12/2004

OTHER PUBLICATIONS

Armour, J.A., et al., "Gross and Microscopic Anatomy of the Human Intrinsic Cardiac Nervous System", The Anatomical Record, Feb. 1997, pp. 289-298, vol. 247, No. 2.

(Continued)

*Primary Examiner* — Michael Peffley
(74) *Attorney, Agent, or Firm* — Taft Stettinius & Hollister LLP

(57) ABSTRACT

An electrosurgical device having a distal tip for creating a lesion on tissue includes a first electrode and a second electrode that are parallel for the delivery of RF energy to tissue. A sensor electrode is provided parallel to and spaced away from the first electrode a different distance than the second electrode. When the sensor electrode and at least one of the first and second electrodes are in contact with tissue. The electrosurgical device can perform at least one of the following: ablating tissue, and sensing at least one selected from the group of voltage, tissue impedance, electrical conduction, conduction time, conduction velocity, and signal phase angle.

13 Claims, 13 Drawing Sheets

U.S. PATENT DOCUMENTS

| | | | |
|---|---|---|---|
| 5,971,980 A | | 10/1999 | Sherman |
| 5,991,650 A | | 11/1999 | Swanson |
| 6,017,358 A | * | 1/2000 | Yoon et al. ............... 606/205 |
| 6,068,629 A | | 5/2000 | Haissaguerre et al. |
| 6,071,281 A | * | 6/2000 | Burnside et al. ............... 606/41 |
| 6,099,524 A | | 8/2000 | Lipson et al. |
| 6,162,216 A | | 12/2000 | Guziak et al. |
| 6,179,836 B1 | | 1/2001 | Eggers et al. |
| 6,197,022 B1 | | 3/2001 | Baker |
| 6,228,080 B1 | | 5/2001 | Gines |
| 6,290,699 B1 | | 9/2001 | Hall et al. |
| 6,332,881 B1 | | 12/2001 | Carner et al. |
| 6,398,779 B1 | | 6/2002 | Buysse et al. |
| 6,464,696 B1 | | 10/2002 | Oyama et al. |
| 6,511,476 B2 | | 1/2003 | Hareyama |
| 6,517,536 B2 | | 2/2003 | Hooven et al. |
| 6,589,237 B2 | | 7/2003 | Woloszko et al. |
| 6,695,839 B2 | | 2/2004 | Sharkey et al. |
| 6,730,082 B2 | | 5/2004 | Messing et al. |
| 6,740,082 B2 | | 5/2004 | Shadduck |
| 6,743,225 B2 | | 6/2004 | Sanchez et al. |
| 6,881,213 B2 | * | 4/2005 | Ryan et al. ............... 606/41 |
| 6,905,498 B2 | * | 6/2005 | Hooven ............... 606/50 |
| 7,549,991 B2 | * | 6/2009 | Lu et al. ............... 606/50 |
| 2002/0032441 A1 | | 3/2002 | Ingle et al. |
| 2002/0128650 A1 | * | 9/2002 | McClurken ............... 606/48 |
| 2003/0055420 A1 | | 3/2003 | Kadhiresan et al. |
| 2003/0181965 A1 | | 9/2003 | Levy et al. |
| 2003/0216733 A1 | | 11/2003 | McClurken et al. |
| 2003/0220639 A1 | | 11/2003 | Chapelon et al. |
| 2004/0030331 A1 | | 2/2004 | Thomas et al. |
| 2004/0082860 A1 | | 4/2004 | Haissaguerre |
| 2004/0082946 A1 | | 4/2004 | Malis et al. |
| 2004/0092926 A1 | | 5/2004 | Hoey et al. |
| 2004/0133251 A1 | | 7/2004 | Altshuler et al. |
| 2004/0181214 A1 | | 9/2004 | Garabedian et al. |
| 2004/0193148 A1 | | 9/2004 | Wham et al. |
| 2005/0030331 A1 | | 2/2005 | Komatsu et al. |
| 2005/0033283 A1 | | 2/2005 | Hooven |
| 2005/0070896 A1 | | 3/2005 | Daniel et al. |
| 2005/0080411 A1 | | 4/2005 | Ouchi |
| 2006/0161149 A1 | | 7/2006 | Privitera et al. |
| 2006/0161151 A1 | | 7/2006 | Privitera et al. |
| 2006/0217701 A1 | | 9/2006 | Young et al. |

OTHER PUBLICATIONS

Blackshear, J.L., et al., "Thoracoscopic Extracardiac Obliteration of the Left Atrial Appendage for Stroke Risk Reduction in Atrial Fibrillation", Journal of Am College Cardiology, Oct. 1, 2003, pp. 1249-1252, vol. 42, No. 7.

Chen, S.A., et al., "Initiation of Atrial Fibrillation by Ectopic Beats Originating from the Pulmonary Veins: Electrophysiological characteristics, Pharmacological responses, and effects of radiofrequency ablation", Circulation 1999, pp. 1879-1886, vol. 100.

Cox, J.L., et al., "Electrophysiologic Basis, Surgical Development, and Clinical results of the Maze Procedure for Atrial Flutter and Atrial Fibrillation", Advances in Cardiac Surgery, 1995, pp. 1-67, vol. 6.

Cox, J.L., et al., "Impact of the Maze Procedure on the Stroke Rate in Patients with Atrial Fibrillation", J. Thorac Cardiovasc Surg., Nov. 1999, pp. 833-840, vol. 118, No. 5.

Cox, J.L., et al., "Current Status of the Maze Procedure for the Treatment of Atrial Fibrillation", Seminars in Thoracic and Cardiovascular Surgery, Jan. 2000, pp. 15-19 vol. 12, No. 1.

Cox, J.L., et al., "New Surgical and Catheter-based Modifications of the Maze Procedure", Seminars in Thoracic and Cardiovascular Surgery, Jan. 2000, pp. 68-73, vol. 12, No. 1.

Cox, J.L., et al., "The Development of the Maze Procedure for the Treatment of Atrial Fibrillation", Seminars in Thoracic and Cardiovascular Surgery, Jan. 2000, pp. 2-14, vol. 12, No. 1.

Damiano, R.J., Jr., et al., "The Long-term Outcome of Patients with Coronary Disease and Atrial Fibrillation undergoing the Cox Maze Procedure", Journal of Thoracic & Cardiovascular Surgery, Dec. 2003, pp. 2016-2021, vol. 126, No. 6.

Deneke, T., et al., "Antiarrhythmic Surgery to Cure Atrial Fibrillation—subgroups and postoperative management", Cardiac Electrophysiol. Rev., Sep. 2003, pp. 259-263, vol. 7, No. 3.

Deneke, T., et al., "Efficacy of an Additional MAZE procedure using cooled-tip radiofrequency ablation in patients with chronic atrial fibrillation and mitral valve disease: A randomized, prospective trial", European Heart Journal, Apr. 2002, pp. 558-566, vol. 23.

Doshi, R., et al., "Relation Between Ligament of Marshall and Adrenergic Atrial Tachyarrhythmia", Circulation, Aug. 24, 1999, pp. 876-883, vol. 100, No. 8.

Feinberg, W., et al., "Prevalence, Age Distribution, and Gender of Patents with Atrial Fibrillation", Arch Intern Med, Mar. 13, 1995, pp. 469-473, vol. 155.

Ganjoo, A.K., "A Novel Approach to the Prevention of Thromboembolism in Atrial Fibrillation", Texas Heart Institute Journal, 2001, p. 163, vol. 28, No. 2.

Garrido, M., et al., "Minimally Invasive Surgery for Atrial Fibrillation: toward a totally endoscopic, beating heart approach", Journal Cardiac Surg, 2004, pp. 216-220, vol. 19.

Gaynor, S., et al., "A Prospective, Single-center Clinical Trial of a modified Cox Maze Procedure with Bipolar Radiofrequency Ablation", Journal of Thoracic & Cardiovascular Surgery, 2004, pp. 535-542, vol. 128, No. 4.

Gillinov, A.M., et al., "Atrial Fibrillation: Current Surgical options & Their Assessment", Ann Thorac Surg, 2002, pp. 2210-2217, vol. 74.

Gillinov, A.M., et al., "Atricure Bipolar Radiofrequency Clamp for Intraoperative Ablation of Atrial Fibrillation", Ann Thorac Surg, 2002, pp. 2165-2168, vol. 74.

Gillinov, A.M., et al., "Bipolar Radiofrequency to Ablate Atrial Fibrillation in Patients Undergoing Mitral Valve Surgery", The Heart Surgery Forum, Feb. 2004, pp. 147-152, vol. 7, No. 2.

Haissaguerre, M., et al., "Spontaneous Initiation of Atrial Fibrillation by Ectopic Beats originating in the Pulmonary Veins", New England Journal Medicine, 1998, pp. 659-666, vol. 339, No. 10.

Haissaguerre, M., et al., "Electrophysiological Breakthroughs from the Left Atrium to the Pulmonary Veins", Circulation, 2000, pp. 2463-2465, vol. 102, No. 20.

Haissaguerre, M., et al., "Electrophysiological End Point for Catheter Ablation of Atrial Fibrillation initiated from Multiple Pulmonary Venous Foci", Circulation, 2000, pp. 1409-1417, vol. 101.

Johnson, W.D., et al., "The Left Atrial appendage: our most lethal human attachment! Surgical Implications", European Journal of Cardio-Thoracic Surgery, 2000, pp. 718-722, vol. 17, No. 6.

Kress, D.C., et al., "Validation of a Left Atrial Lesion Pattern for Intraoperative Ablation of Atrial Fibrillation" Ann Thorac Surg, 2002, pp. 1160-1168, vol. 73.

Lloyd-Jones, D.M., et al., "Lifetime Risk for Development of Atrial Fibrillation—The Framingham Heart Study", Circulation, 2004, pp. 1042-1046, vol. 110.

Martin, A., et al., "Five-year follow-up of 101 Elderly Subjects by means of Long-term Ambulatory Cardiac Monitoring", European Society of Cardiology, 1984, pp. 592-596, vol. 5.

McCarthy, P.M., et al., "The Cox-Maze Procedure—The Cleveland Clinic Experience", Seminars in Thoracic & Cardiovascular Surgery, Jan. 2000, pp. 25-29, vol. 12, No. 1.

Melo, J.Q., et al., "Atrial Ablation for the Surgical Treatment of Atrial Fibrillation: Principles and Limitations", Journal Cardiac Surgery, 2004, pp. 207-210, vol. 19.

Mokadam, N.A., "A Prospective Multicenter Trial of Bipolar Radiofrequency Ablation for Atrial Fibrillation: Early Results", Ann Thorac Surg, 2004, pp. 1665-1670, vol. 78.

Nademanee, K., et al., "A New Approach for Catheter Ablation of Atrial Fibrillation: Mapping of the Electrophysiologic Substrate", Journal of Amer College of Cardiology, Jun. 2, 2004 pp. 2044-2053, vol. 43, No. 11.

Nakagawa, H., et al., "Catheter Ablation of Cardiac Autonomic Nerves for Prevention of Atrial Fibrillation in a Canine Model", Heart Rhythm, May 2004, vol. 1 S10 (Abstract 31).

Pappone, C., et al., "Circumferential Radiofrequency Ablation of Pulmonary Vein Ostia: A New Anatomic Approach for Curing Atrial Fibrillation", Circulation, 2000, pp. 2619-2628, vol. 102.

Pappone, C., et al., "Atrial Electroanatomic Remodeling after Circumferential Radiofrequency Pulmonary Vein Ablation: Efficacy of an Anatomic Approach in a Large cohort of patients with Atrial Fibrillation", Circulation, 2001, pp. 2539-2544, vol. 104.

Pappone, C., et al., "Pulmonary Vein Denervation Enhances Long-term benefit after Circumferential Ablation for Paroxysmal Atrial Fibrillation", Circulation, 2004 pp. 327-334, vol. 109.

Patterson, E., et al., "Reentrant Tachycardias Elicited by Acetylcholine from Isolated Canine Pulmonary Veins", Circulation, 2003, p. IV-149, vol. 108, (Abstract).

Peters, N., et al., "Atrial Fibrillation: strategies to control, combat, and cure", Lancet, 2002, pp. 593-603, vol. 359.

Prasad, S.M., et al., "Epicardial Ablation on the Beating Heart: Progress Towards an Off-Pump Maze Procedure", Heart Surgery Forum, 2001 pp. 100-104, vol. 5.

Prasad, S.M., et al., "Chronic transmural atrial ablation by using bipolar radiofrequency energy on the beating heart", Journal of Thoracic & Cardiovascular Surgery, 2002, pp. 708-713, vol. 124.

Prasad, S.M., et al., "Physiological Consequences of Bipolar Radiofrequency Energy on the Atria and Pulmonary Veins: A Chronic Animal Study", Ann Thorac Surg, 2003, pp. 836-842, vol. 76.

Prasad, S.M., et al., "The Cox Maze III procedure for atrial fibrillation: Long-term efficacy in patients undergoing lone versus concomitant procedures", Journal Thoracic Cardiovascular Surgery, Dec. 2003, pp. 1822-1828, vol. 126, No. 6.

Raman, J., et al., "Surgical Radiofrequency ablation of both Atria for Atrial Fibrillation: Results of a multicenter trial", Journal of Thoracic Cardiovasc Surg, Nov. 2003, pp. 1357-1366, vol. 126, No. 5.

Ryan, W.H., et al., "Experience with Various Surgical Options for the Treatment of Atrial Fibrillation", Heart Surgery Forum, 2004, pp. 1013-1017, vol. 7, No. 4.

Saad, E.B., et al., "Pulmonary Vein Stenosis after Catheter Ablation of Atrial Fibrillation: Emergence of New Clinical Syndrome", Annals of Internal Medicine, Apr. 2003, pp. 634638, vol. 138, No. 8.

Scherlag, B.J., et al., "Stimulation of the 'Sino-Atrial' Fat Pad converts focal Pulmonary Vein firing into Atrial Fibrillation in the Dog Heart", Circulation, 2003, p. IV-85, vol. 108 (Abstract).

Sie, H.T., et al., "Long-term results of Irrigated Radiofrequency Modified Maze Procedure in 200 Patients with Concomitant Cardiac Surgery: Six Years Experience", Ann Thorac Sum., Feb. 2004, pp. 512-516 (discussion pp. 516-517), vol. 77, No. 2.

Sie, H.T., et al., "Radiofrequency modified Maze in Patients with Atrial Fibrillation undergoing Concomitant Cardiac Surgery", Journal of Thoracic and Cardiovascular Surgery, 2001, pp. 249-256, vol. 122.

Sundt, T.M., III, et al., "The Maze Procedure for Cure of Atrial Fibrillation", Cardiology Clinics, Nov. 1997, pp. 739-748, vol. 15, No. 4.

Tomita, T., et al., "Role of Autonomic Tone in the Initiation and Termination of Paroxysmal Atrial Fibrillation in Patients without Structural Heart Disease", Journal of Cardiovasc Electrophysiology, Jun. 2003, pp. 559-564, vol. 14, No. 6.

Treseder, A.S., et al., "Atrial Fibrillation and Stroke in Elderly Hospitalized Patients", Age and Ageing, 1986, pp. 89-92, vol. 15.

Wharton, J.M., "Ablation of Atrial Fibrillation: a procedure come of age?", Current Control Trials Cardiovascu Med, 2001, pp. 67-70, vol. 2, No. 2.

Williams, M.R., et al., "Alternative Energy Sources for Surgical Atrial Ablation", Journal Card. Surg., 2004, pp. 201-206, vol. 19.

Wu, T., et al., "Pulmonary Veins and Ligament of Marshall as Sources of Rapid Activations in a Canine Model of Sustained Atrial Fibrillation", Circulation, 2001, pp. 1157-1163, vol. 103.

Yasuda, T., et al., "Predictors of Successful Catheter Ablation for Atrial Fibrillation Using the Pulmonary Vein Isolation Technique", Journal Cardiology, 2004, pp. 53-58, vol. 44 No. 2.

Yuda, S., et al., "Long-term Follow-up of Atrial Contraction after the Maze Procedure in Patients with Mitral Valve Disease", Journal American College Cardiolog, 2001, pp. 1622-1627, vol. 37.

Extended European Search Report issued in EP Application 07 252279.01 dated Nov. 20, 2007.

Partial European search report, issued in EP application No. 07252279.0, dated Sep. 5, 2007.

PCT International Search Report, PCT/US2005/044201, International Filing Date Jun. 12, 2005, mailed May 5, 2006.

PCT Written Opinion of the International Searching Authority, PCT/US2005/044201, International Filing Date Jun. 12, 2005.

PCT International Search Report, PCT/US20071004908, Feb. 23, 2007.

PCT Written Opinion of the International Searching Authority, PCT/US2007/004908, Feb. 23, 2007.

* cited by examiner

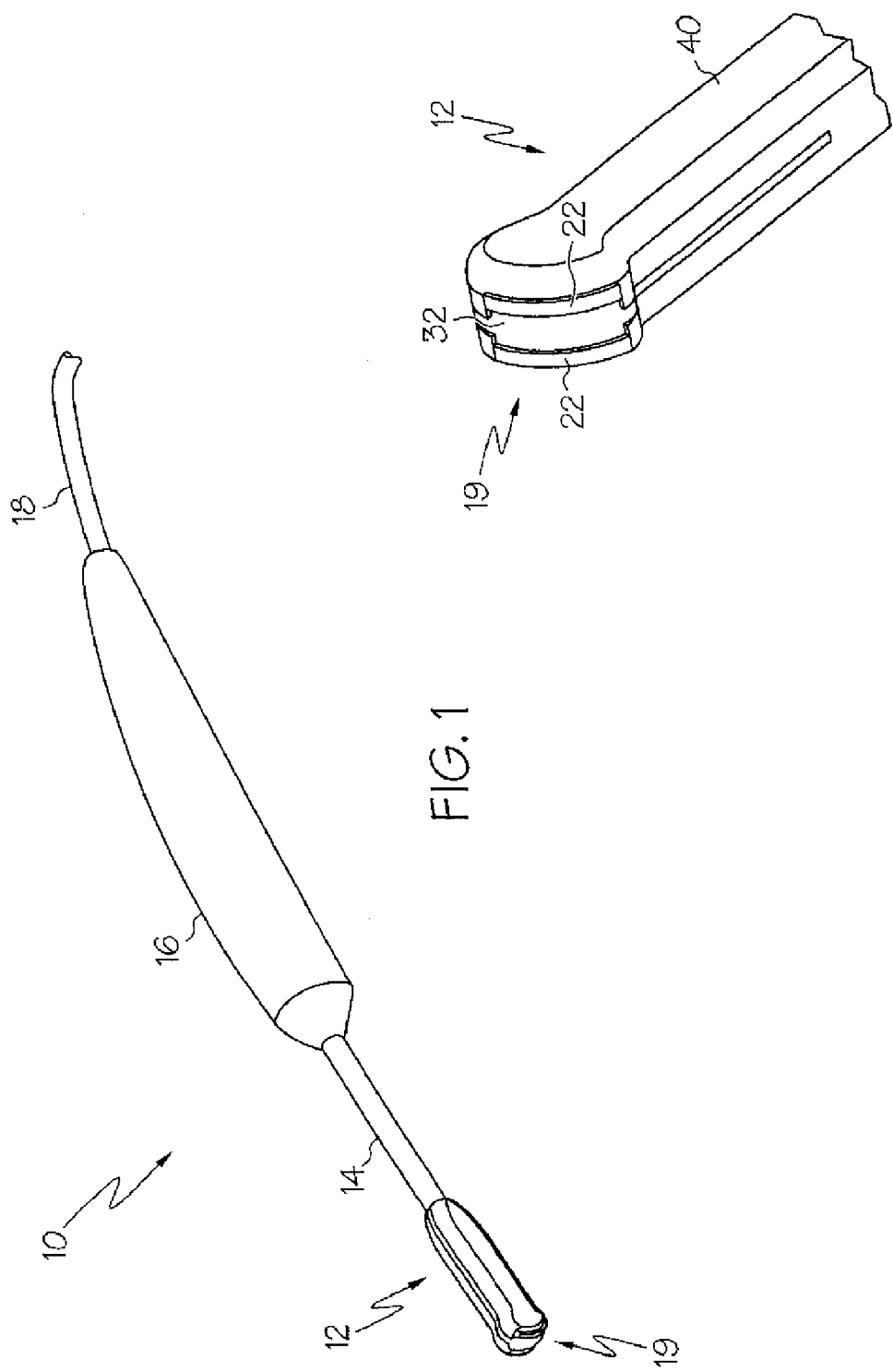

ABLATION DEVICE WITH SENSOR

PRIORITY INFORMATION

This application is a division of U.S. patent application Ser. No. 11/457,919 filed Jul. 17, 2006, now U.S. Pat. No. 8,034,051, which is a CIP of U.S. patent application Ser. No. 11/363,707 filed Feb. 28, 2006, now U.S. Pat. No. 7,828,795, titled "Surgical Ablation and Pacing Device" to Privitera et al., claiming priority to U.S. Provisional Patent Application Ser. No 60/699,679, filed Jul. 15, 2005, titled "Ablation Device With Sensor" to Privitera et al., each of which is hereby incorporated by reference in their entirety herein.

BACKGROUND OF THE INVENTION

The present invention relates to surgical instruments, with examples relating to cardiovascular pacing devices, systems for controlling such devices, and methods for using such devices. "Surgery" generally refers to the diagnosis or treatment of injury, deformity, disease, or other conditions. In a variety of surgical procedures, it may be desirable to stimulate the heart using a pulsed current via a bi-polar probe or other device. Such pacing may be desirable, for instance, after an ablation procedure has been performed on a heart in order to determine how successful the ablation was. Accordingly, it may be desirable to provide a device operable for use in both ablation and pacing procedures. The foregoing examples are merely illustrative and not exhaustive. While a variety of devices have been used to pace the heart of a patient or perform other procedures, it is believed that no one prior to the inventors has previously made or used an invention as described in the appended claims.

The present invention relates to surgical instruments, with examples relating to bi-polar ablation devices in combination with a variety of sensors, systems useable with such devices, and methods of using such devices. Surgery generally refers to the diagnosis or treatment of injury, deformity, or disease. In a variety of surgical procedures, it is desired to ablate tissue or cause lesions in tissue. Some examples of such procedures include, without limitation, electrical isolation of cardiac tissue to treat atrial fibrillation, ablation of uterine tissue associated with endometriosis, ablation of esophageal tissue associated with Barrett's esophagus, ablation of cancerous liver tissue, and the like. The foregoing examples are merely illustrative and not exhaustive.

Atrial fibrillation is an abnormality of the electrical system of the heart. Normally, the heartbeat is triggered by an electrical impulse which starts in the Sinoatrial (SA) node structure which resides in the right atrium and acts as the "pacemaker" of the heart. The electrical signal to contract the heart starts in the SA node and normally moves evenly across the atrium, triggering it to contract all at once. The impulse then travels across the atrioventricular (AV) node and triggers the ventricles (the main pumping chambers of the heart) to contract. This is called sinus rhythm. Atrial fibrillation occurs when this electrical impulse no longer travels in the normal manner and causes the atrium to contract in an un-coordinated manner, causing irregular fibrillation. The MAZE Procedure is a surgical procedure used by Cardiothoracic surgeons to create scar tissue barriers in the heart as a way to block the unwanted electrical signals that cause erratic heartbeats or atrial fibrillation. By way of example, this procedure can be performed by surgical incision and suturing, a cryosurgical system, or energy ablation devices such as a monopolar pen with saline, or a bipolar pen. The Maze procedure has been widely accepted as the gold standard of care in the treatment of atrial fibrillation with a very high success rate. This surgical procedure can be performed openly, as a minimally invasive procedure or in a modified form such as the Mini Maze procedure. The MAZE or MINI MAZE surgical procedure using an electrosurgical device begins with a voltage mapping procedure that uses a pair of tissue contact electrodes attached to a sensor such as an echogram machine to map the location of natural electrical signals that stimulate the heart to beat. Once the location of the impulses are found and mapped, the surgeon replaces the echogram machine and sensing electrodes with a pair of pacing electrodes. The pacing electrodes are held spaced apart a preset distance and are placed into contact with tissue at a number of the mapped positions. At each position the pacing electrodes are energized to stimulate the heart. If no response occurs, the voltage is increased, and the stimulation is resupplied until the heart reacts. This determines the stimulation threshold voltage at each site. The stimulation locations, stimulation responses, and threshold voltages are noted on the heart map and are used to identify the location of the specific nerves that are responsible for the irregular heartbeat. Once the heart has been mapped, the pacing electrodes are removed and replaced with one or more electrosurgical devices that apply RF energy to the heart to create lesions therein. RF energy is applied via the electrodes to create one or more coagulated lesions on the heart. The ablation electrodes can also be used to monitor tissue effects such as impedance during ablation. After the lesions of cauterized tissue are placed onto the heart, the electrosurgical device or devices are removed. The efficacy of the lesion is sensed by placing the pair of echogram electrodes across or onto the lesion area to sense continuity across the lesion. If there is no continuity across the lesion, the lesion was successful. Alternately, or in addition to the echogram electrodes, the pair of pacing electrodes can be placed across the lesions to apply stimulation voltages. These stimulation voltages can also be used as an alternate check of the efficacy of the lesion. If the stimulation voltages fail to stimulate across the lesions, the lesion was successful.

At present, there are no known electrosurgical instruments that can meet all of the needs outlined above. These and other advantages will become more apparent from the following detailed description and drawings

BRIEF SUMMARY OF THE INVENTION

In accordance with the present invention, there is provided an electrosurgical device having a distal tip for creating a lesion on tissue. The electrosurgical device includes a first pole electrode on the distal tip for the delivery of RF energy to tissue. A second pole electrode is provided on the distal tip parallel to and spaced away from the first electrode a first distance, the second pole electrode for the delivery of RF energy to tissue. And, a sensor electrode is located on the distal tip parallel to and spaced away from the first pole electrode a second distance. When the sensor electrode and at least one of the first pole electrode and the second pole electrode are in contact with tissue, the sensor electrode enables a sensor to senses at least one selected from the group of voltage, tissue impedance, electrical conduction, conduction time, conduction velocity, and signal phase angle.

Also in accordance with the present invention, there is provided an electrosurgical device having a distal tip for creating a lesion on tissue. The electrosurgical device has a first pole electrode on the distal tip for the delivery of RF energy to tissue; and a second pole electrode on the distal tip parallel to and spaced away from the first electrode a first distance, the second pole electrode also for the delivery of RF energy to tissue. A sensor electrode is included on the tip for sensing at least one selected from the group of voltage, tissue impedance, electrical conduction, conduction time, conduction velocity, and phase angle measured between any two of the sensor, the first pole electrode, and the second pole electrode. And, an electrode gap adjustment mechanism is included for adjusting the first distance between the first pole electrode and the second pole electrode to a distance optimized for at least one selected from the group of lesion width, lesion depth, voltage sensing across a lesion, electrical conduction across a lesion, electrical conduction velocity across a lesion, and phase angle of a signal measured across a lesion.

Also in accordance with the present invention, there is provided an method of creating a lesion on tissue with an electrosurgical device that includes providing an electrosurgical system. The electrosurgical system has a generator, a handpiece having at least a first electrode and a second electrode on a distal tip, and, at least one sensor operably connected to the at least first electrode and second electrode, the at least one sensor selected from at least one of the group of an impedance sensing circuit, a pacing monitor, an impedance monitoring system and an electrogram machine. The first step of the method comprises ablating tissue with the first electrode and the second electrode placed to create a lesion therebetween. The second step comprise sensing the effectivity of the lesion with the first electrode and second electrodes of the electrosurgical device.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 1 illustrates a perspective view of an example of an ablation device;

FIG. 2 illustrates a perspective detailed view of the head of the ablation device of FIG. 1;

DETAILED DESCRIPTION OF THE INVENTION

Figure 3:
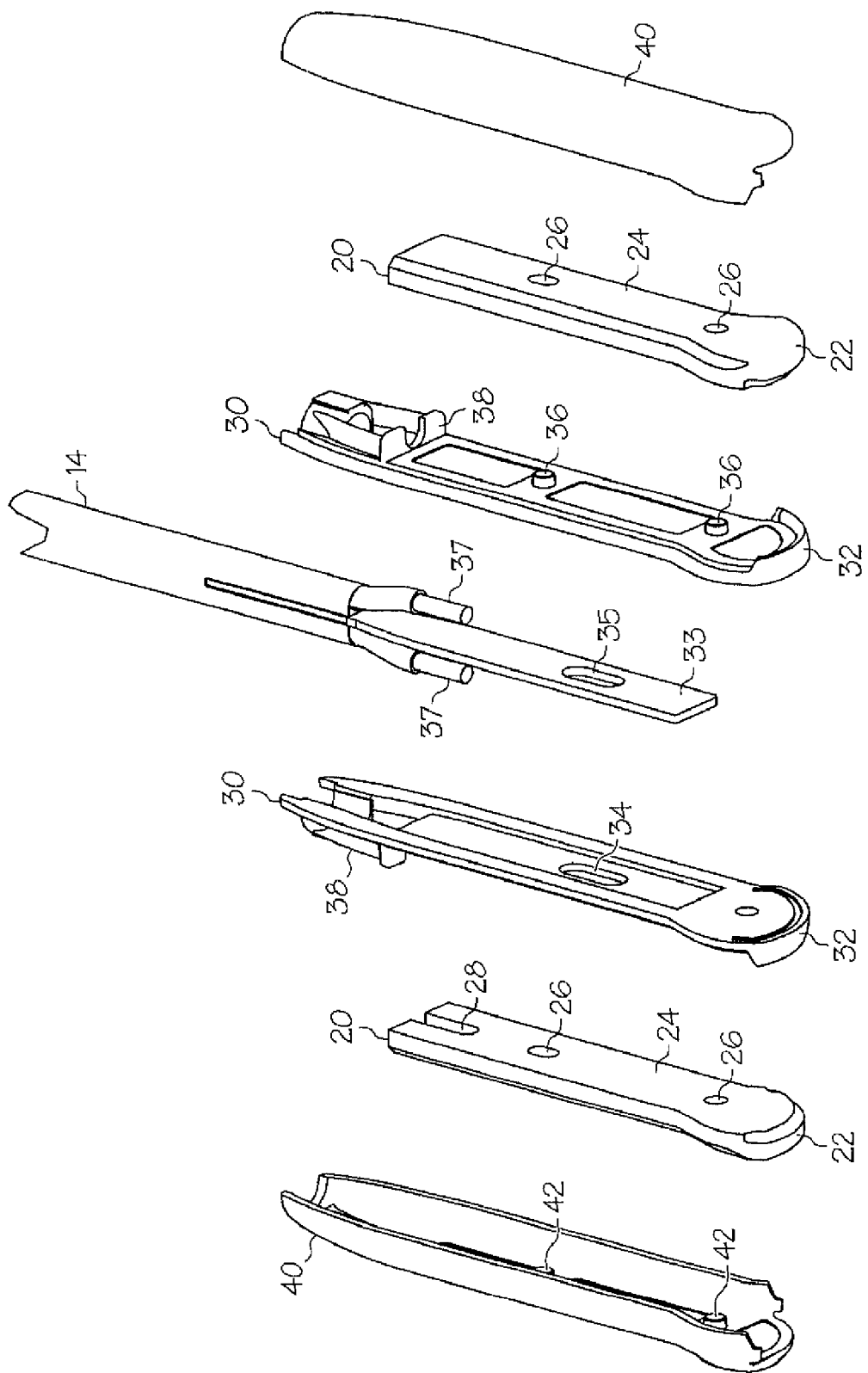
FIG. 3 illustrates an exploded view of the head of the ablation device of FIG. 1.

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

FIG. 1 illustrates an example of an ablation device 10. The ablation device 10 in this embodiment comprises a handheld wand. The ablation device 10 includes a head 12 connected to the distal end of a shaft 14, and a handle 16 connected to the proximal end of the shaft 14. As shown here, the shaft 14 is straight and substantially rigid; however, flexible, curved, malleable, articulated, or other shafts could also be used depending on a variety of considerations. A power source (not shown) is connected to the cord 18 in the present example.

FIG. 2 illustrates a more detailed view of the head 12 of the ablation device 10. The head 12 includes a tip portion 19 having two electrodes 22, which are capable of being energized with bi-polar energy. In the present example, each electrode 22 includes a smooth surface area for contacting tissue. Each electrode 22 is slender in the sense that the length of the tissue contacting surface is at least 4 times its width. As shown in the present example, the length is between about 5 to 7 times the width. Of course, any other suitable configuration for electrodes 22 may be used.

The electrodes 22 in this example are substantially parallel to one another, and as shown here the electrodes 22 are spaced between about 2 to 4 mm from one another. It will be appreciated, however, that these dimensions are merely exemplary. An electrically insulative surface 32 is interposed between the electrodes 22. In this example, the surface 32 is convex between the electrodes 22, distally extending about 0.01 inches from the lateral plane between the electrodes 22. Again, though, any other suitable dimensions may be used. As shown in the figures, a portion of the tip portion 19 of the head 12 is curved along the transverse axis. In the present example, the curved end is an arc with a radius between 0.19 and 0.21 inches. The electrodes 22 and surface 32 have similar curves. An electrically insulative sheath 40 covers other portions of the head 12. Other suitable configurations will be apparent to those of ordinary skill in the art.

Figure 4:
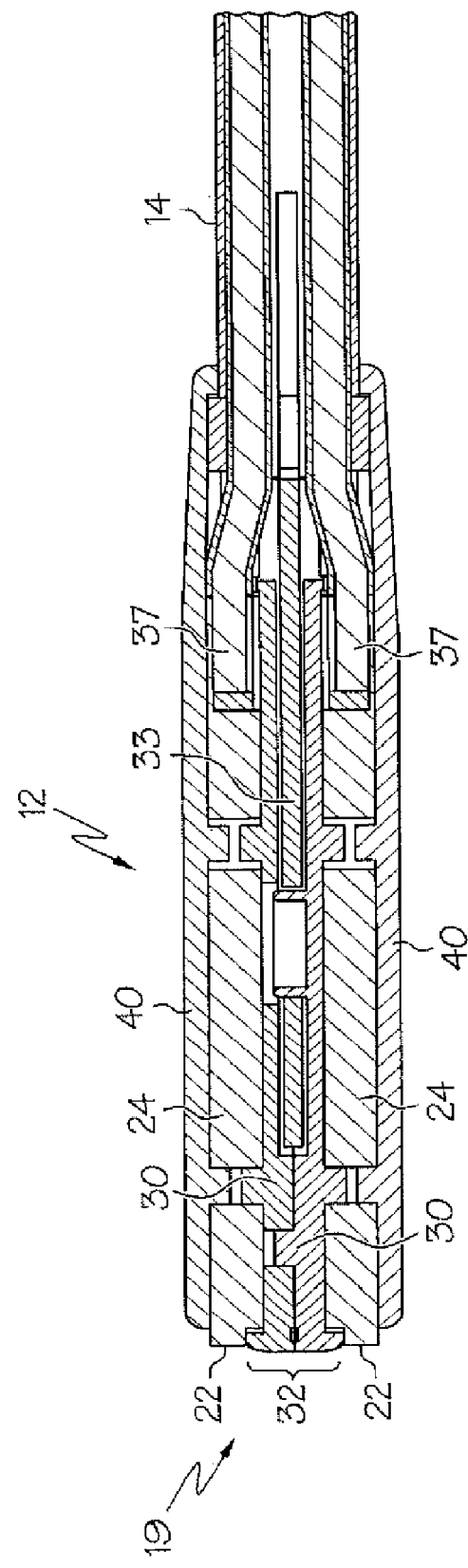
FIG. 4 illustrates a cross-sectional view of the head of the ablation device of FIG. 1.

FIGS. 3 and 4 illustrate some component parts of the head 12 and some related structures. A rib 33 extends distally from the shaft 14. Electrical wires in communication with the cord 18 pass through the shaft 14 and end with electrical terminals 37. A pair of electrical insulators 30 laterally connects to either side of the rib 33. The distal tips of the insulators 30 define the insulative surface 32. A post (hidden in this view) on the right insulator 30 mates with the holes 35, 34. A receiving structure 38 is dimensioned to hold the terminals 37 in their desired positions.

Two conductors 20 laterally connect with the insulators 30. In the present example, each conductor 20 is a contiguous and unitary part; however, two or more components could form the conductor 20. Also in this example, each conductor 20 is a homogeneous material. Each conductor 20 includes an electrode 22 and heat sink 24. Each conductor has a recess 28 dimensioned to snugly receive the corresponding terminal 37, thus facilitating electrical contact with the terminal 37. The sheath 40 covers the assembled head 12. Posts 42, 36 mate with the holes 26 in the conductor 20 to facilitate and maintain alignment of the assembly. The distal ends of the conductors 20, bounded by the surface 32 and the sheath 40, define the surface areas of the electrodes 22.

The conductor 20 in this example is electrically conductive, thus facilitating the flow of current from the terminal 37 to the electrode 22. The conductor 20 in this example is also thermally conductive, thus facilitating the flow of heat from the electrode 22 to the heat sink 24. Some suitable materials for the conductor 22 include, without limitation, copper, silver, gold, platinum, titanium, aluminum, beryllium, nickel, and the like. In one variation, the heat sink 24 is copper while the electrode 22 is gold plated. The heat sink 24 has a volume, which in this example is the volume of the conductor 20. Preferably, the ratio of tissue contacting surface area of the electrode 22 to volume of the heat sink 24 is less than about 3 $in^2/in^3$. In the present example, the ratio is less than about 1 $in^2/in^3$. Any other suitable ratio may be used.

One illustrative use of the device 10 is during surgery to ablate tissue. The surface area of the electrodes 22 are placed in contact with the tissue surface. The electrodes 22 are energized with bi-polar energy by connecting the device 10 to an electric power source. As one with ordinary skill in the art will readily appreciate, RF energy is transmitted to the tissue through the electrodes 22, thus heating the tissue until ablated and a desired lesion is formed in the tissue. Optionally, the head 12 may be swiped over the tissue surface, either laterally or transversely, while maintaining the electrodes 22 in contact with the tissue to ablate larger areas or to ablate the tissue in a desired pattern. Other methods of using the device 10 will be apparent to those of ordinary skill in the art. The heat sink 24 draws heat away from the tissue during the ablation process, thus reducing the temperature elevation of the tissue surface. The temperature reduction may provide the benefit (among other benefits) of facilitating deeper and more controlled lesions, including, when desired, transmural lesions through a tissue wall.

It will be appreciated that creating an ablation in tissue with the device 10 may provide a barrier to electrical signals that may otherwise be communicated across the ablated tissue. By way of example only, such a barrier may provide a form of treating atrial fibrillation or other conditions. For instance, where atrial fibrillation is caused by aberrant or erratic electrical signals coming from one or more pulmonary veins to one or both atria of the heart, an ablation may be provided as a barrier between such veins and atria. In other words, one or more ablations may serve to electrically isolate one or more pulmonary veins from the atria. By preventing or substantially preventing aberrant or erratic electrical signals coming from one or more pulmonary veins from reaching the atria, a more desirable sinus rhythm may be maintained. Of course, any other tissues or anatomical structures may be ablated for any reason.

Figure 5:
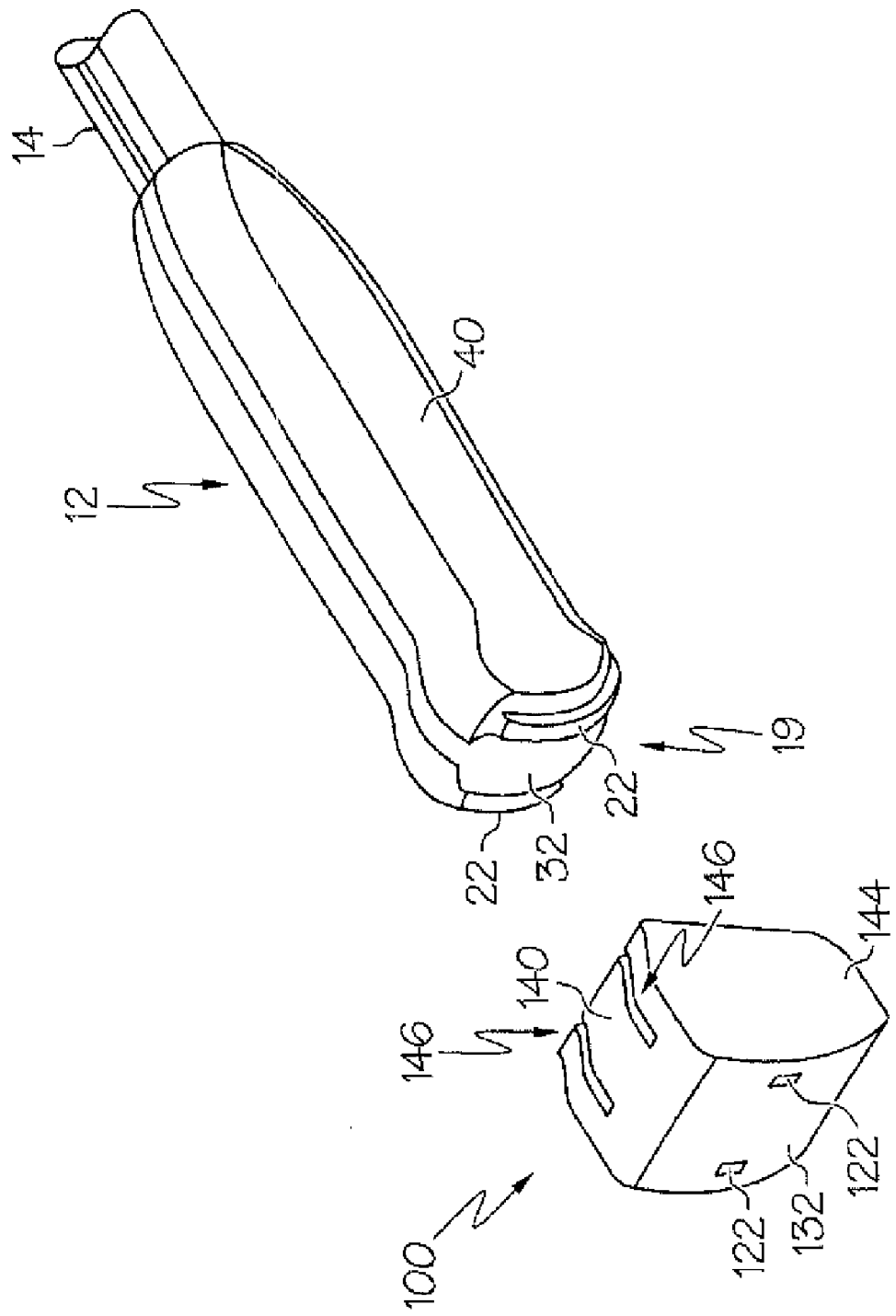
FIG. 5 illustrates a perspective view of an example of a pacing tip configured to engage the head of the ablation device of FIG. 1.
Figure 6:
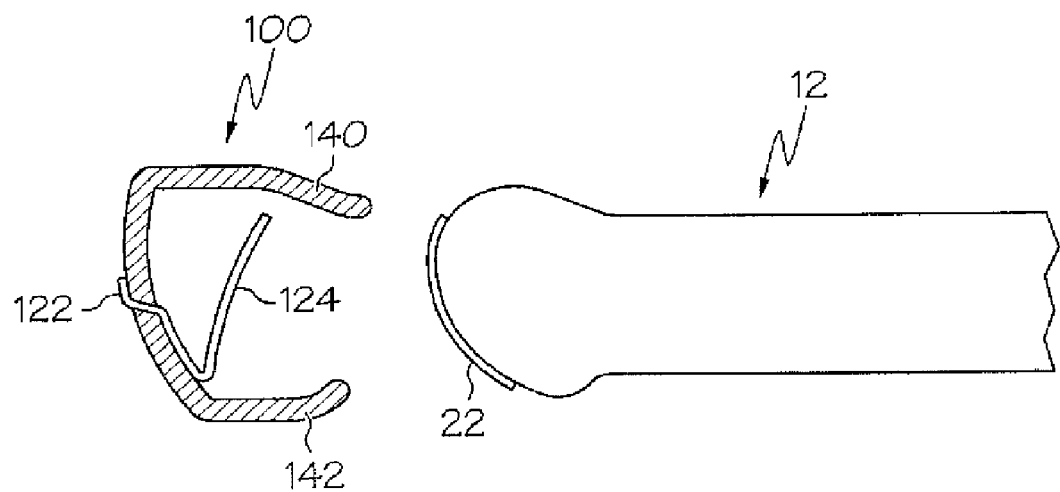
FIG. 6 illustrates a partial cross-sectional view of the pacing tip of FIG. 5 prior to engagement with the head of the ablation device of FIG. 1.
Figure 7:
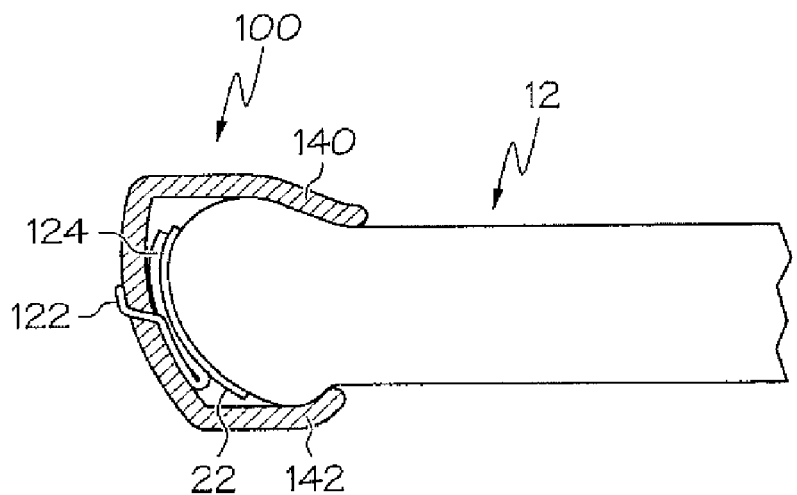
FIG. 7 illustrates a partial cross-sectional view of the pacing tip of FIG. 5 engaged with the head of the ablation device of FIG. 1.

FIGS. 5 through 7 illustrate a pacing tip 100 configured to engage the head 12 of the device 10. The pacing tip 100 comprises a pair of electrodes 122, an insulative face 132, an upper clipping portion 140, a lower clipping portion 142, and a pair of sidewalls 144 extending between the upper and lower clipping portions 140, 142. The upper clipping portion 140 comprises a pair of gaps 146, which are configured to permit some motion of upper clipping portion 140 relative to sidewalls 144. Such gaps 146 may facilitate engagement and disengagement of pacing tip 100 with the head 12 of the device 10. Each of the electrodes 122 comprises a respective leaf spring portion 124. As shown in FIGS. 6 and 7, the upper and lower clipping portions 140, 142 are configured to "snap on" to the head 12 of the device 10. Each of the leaf spring portions 124 is configured to engage a respective electrode 22 on the head 12 when the pacing tip 100 is snapped onto the head 12. The leaf spring portions 124 are further configured to provide electrical continuity between the electrodes 22 of the head 12 and the electrodes 122 of the pacing tip 100. It will be appreciated that, to the extent that the electrodes 122 of the pacing tip 100 are not aligned with the electrodes 22 of the head 12, the leaf spring portions 124 may still be configured to provide electrical continuity between the electrodes 122, 22. It will also be appreciated that leaf spring portions 124 are not necessarily required, and that any other suitable structures or features configured to provide electrical continuity between the electrodes 122, 22 may be used.

As shown, the electrodes 122 of the pacing tip 100 are spaced apart further than the electrodes 22 of the head 12. For instance, the electrodes 122 may be spaced anywhere from approximately 2 mm apart to approximately 5 mm apart. In the present example, the electrodes are spaced apart approximately 3 mm. Of course, any other suitable electrode 122 spacing may be used. In addition, the electrodes 122 of the pacing tip 100 of the present example are each relatively narrower and shorter than the corresponding electrodes 22 on the head 12. It is contemplated that a variety of pacing tips 100 may be made and used having a variety of electrode 122 spacings, dimensions, and configurations. A few of such alternative electrode 122 configurations will be described in greater detail below. It is further contemplated that such a variety of pacing tips 100 may all be similarly engageable with the head 12, providing a modular selection of pacing tips 100 available for user selection based on ideal electrode 122 configurations for a particular use or based on other considerations.

In one exemplary use, the pacing tip 100 is secured to the head 12 of the device 10, and the electrodes 122 are positioned on tissue adjacent the pulmonary veins of a patient's heart. As will be described in greater detail below, a pacing signal is then sent to the tissue via the electrodes 122 until an effect on the heart of the patient (e.g., an increase in the heartbeat rate) is observed. The pacing tip 100 is then removed from the head 12, and the pacing tip 100 and head 12 are both cleaned. Next, the device 10 is used to ablate tissue between the pulmonary veins and heart atria (e.g., using electrodes 22 as described above), providing an ablation line in the tissue. Of course, such a "line" need not be straight, and may comprise a curve or pattern, etc. The head 12 is then cleaned again, and the pacing tip 100 is snapped back onto the head 12 of the device 10. With the pacing tip 100 secured to the head 12, the electrodes 122 are again positioned on tissue adjacent the pulmonary veins of the patient's heart. For instance, the electrodes 122 may be positioned in approximately the same location at which they were positioned previously during the prior act of pacing. The pacing signal that had previously produced an observed effect on the heartbeat rate of the patient is again sent to the tissue via the electrodes 122. To the extent that the same signal no longer produces the same effect, the success of the ablation may be confirmed. In other words, this subsequent act of pacing may be used to verify whether the ablated tissue provides sufficient electrical resistance. Conversely, if the same pacing signal produces the same effect that it had before (or some other unsatisfactory effect), the ablation steps may be performed again, and then checked again with the pacing steps until satisfactory results are achieved.

It will be appreciated that any of the foregoing steps may be varied, substituted, supplemented, or omitted. For instance, the initial step of pacing may be omitted. In addition, the second act of pacing may comprise the use of a pacing signal having properties that differ from the prior pacing signal (e.g., higher voltage, higher frequency, etc.). The success of an ablation may also be checked or verified using any suitable techniques other than pacing. Still other ways in which the exemplary method may be modified will be apparent to those of ordinary skill in the art.

As noted above, the device 10 may be used in a pacing mode to deliver a low frequency signal via the electrodes 122 to verify that the ablation has provided a satisfactory conduction block or other sufficient amount of electrical resistance in the tissue. By way of example only, such pacing may include the stimulation of the tissue with a pulsed current via the electrodes 122 of the pacing tip 100. In the context of use on heart tissue, if the heart does not respond to an initial pulsed current, the current may be increased until the heart responds to the stimulation. A response to stimulation may be detected using, by way of example only, an ECG, visual observation to detect an increase in heart rate, and/or by using any other suitable technique. Accordingly, it will be appreciated that, after placing an ablation line on the tissue, the user may verify sufficient conduction block by showing that the heart does not respond to the stimulus when placed en the other side of the electrically isolated line. By way of example only, the pacing signal may be anywhere from between approximately 1.0 to 2.5 Hz, at approximately 0.5 to 10.0 volts, with a current ranging from approximately 0.1 mA to 20.0 mA, at a 500 ohm load. In one embodiment, a signal is varied between approximately 1 to 2 Hz and approximately 0.5 to 2.0 volts. Other signal parameters suitable for pacing may be used, as will be apparent to those of ordinary skill in the art.

While the present example discusses the use of the device 10 to perform pacing, it will be appreciated that a variety of other devices may be used to perform pacing. In particular, like device 10, these other devices may be capable of performing both ablation and pacing, with or without modification of the structure of such devices. For instance, a bi-polar clamp used for ablation may also be used for pacing. By way of example only, any of the bi-polar clamps disclosed in U.S. Non-Provisional patent application Ser. No. 11/254,075, entitled "Articulated Bi-Polar Clamp," filed Oct. 19, 2005, the disclosure of which is incorporated by reference herein, may be used to perform pacing in a manner similar to that described above.

Figure 8:
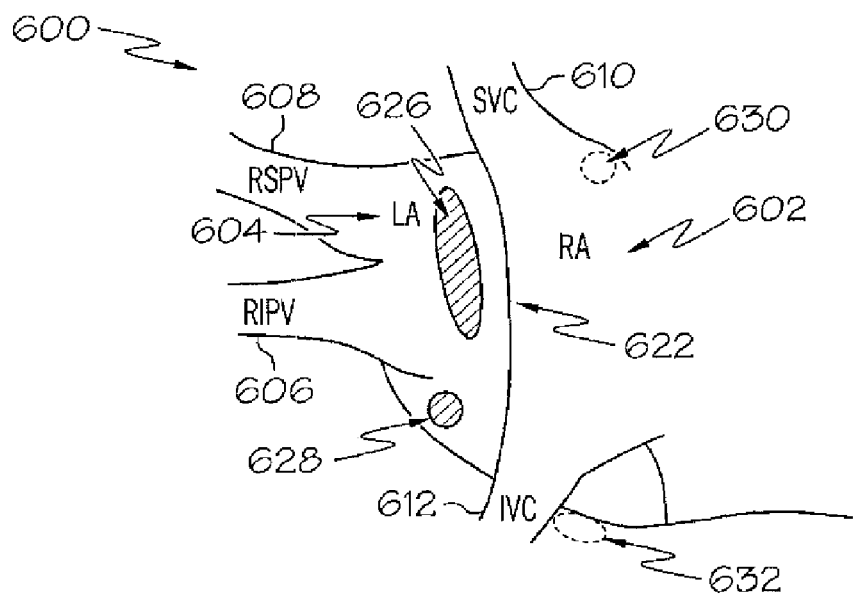
FIG. 8 illustrates a partial left lateral view of a patient's heart.
Figure 9:
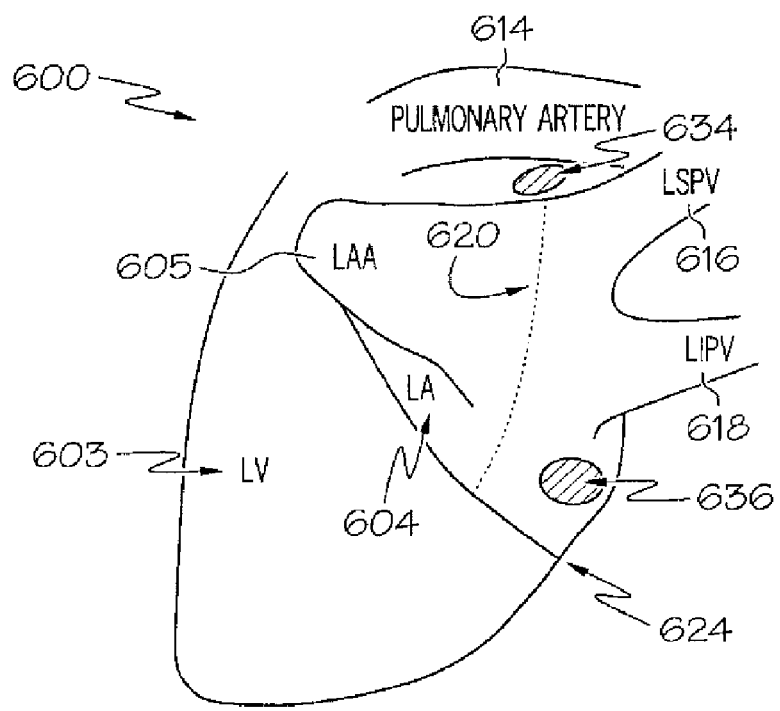
FIG. 9 illustrates a partial right lateral view of the heart of FIG. 8.

In a high frequency stimulation mode, the device 10 may be used to identify specific anatomical structures, including but not limited to terminations of the sympathetic and parasympathetic nervous systems located in the fat pads on and around the heart. Examples of such structures are shown in FIGS. 8 and 9, which depict portions of a heart 600. In particular, FIG. 8 shows the right atrium 602 with superior vena cava 610 and inferior vena cava 612; the left atrium 604 with right superior pulmonary vein 608 and right inferior pulmonary vein 606; and Waterston's groove 622. FIG. 9 shows the left ventricle 603, the left atrium 604 with left atrial appendage 605, left superior pulmonary vein 616, left inferior pulmonary vein 618, and Ligament of Marshall 620; and pulmonary artery 614. FIGS. 8 and 9 also depict autonomic ganglia, which are present on the epicardial surface of the right atrium 602 and left atrium 604, and comprise the anterior right ganglionated plexus 626, the superior left ganglionated plexus 634, the inferior right ganglionated plexus 628, the inferior left ganglionated plexus 636, the SVC-RA ganglionated plexus 630, and the crux ganglionated plexus 624. As shown, the anterior right ganglionated plexus 626 is located anterior to the right pulmonary veins 606, 608. The superior left ganglionated plexus 634 is located between the superior surface of the left atrium 604 (near the base of the left superior pulmonary vein 616) and the pulmonary artery 614, in close proximity to the site of insertion of the Ligament of Marshall 620 into the pericardium. The inferior right ganglionated plexus 628 is located inferior to the right inferior pulmonary vein 606, at the bottom of the antrum of the right pulmonary veins 606, 608. The inferior left ganglionated plexus 636 is located inferior to the left inferior pulmonary vein 618, at the bottom of the antrum of the left pulmonary veins 616, 618. The SVC-RA ganglionated plexus 630 is located at the medial aspect of the junction of the superior vena cava 610 and right atrium 602. The crux ganglionated plexus 624 is located at the crux of the heart 600 between the right atrium 602 and left atrium 604, close to the coronary sinus ostium (not shown) and inferior vena cava 612. Those of ordinary skill in the art will appreciate that the locations of the ganglionated plexi 626, 628, 630, 632, 634, 636 may vary somewhat relative to FIGS. 8 and 9 for a given patient. Furthermore, it will be appreciated that, using high frequency stimulation, the device 10 may be used to identify or localize these ganglionated plexi 626, 628, 630, 632, 634, 636.

By way of example only, the stimulation signal used to identify the ganglionated plexi 626, 628, 630, 632, 634, 636 may be anywhere from between approximately 13 to 25 Hz, at approximately 1 to 12 volts, with a current ranging from 2 to 24 mA, at a 500 ohm load, with a pulse width between approximately 0.02 and 9 ms. In one embodiment, a signal is varied between approximately 15 to 20 Hz at approximately 10 volts. Other signal parameters suitable for stimulation may be used, as will be apparent to those of ordinary skill in the art. When administered close to or adjacent to a ganglionated plexus 626, 628, 630, 632, 634, or 636, a stimulation signal may produce a vagal response identified by a marked lengthening of the R-R interval during atrial fibrillation.

Having identified any of the ganglionated plexi 626, 628, 630, 632, 634, 636 using stimulation with the device 10, the device 10 may then be used to ablate any or all of the identified ganglionated plexi 626, 628, 630, 632, 634, 636. Endocardial ablation at or near such sites may eliminate the vagal response to stimulation and high frequency fractionated potentials in such areas during stimulation. Ablation of the Ligament of Marshall 620 may also reduce the likelihood of atrial fibrillation. Other suitable ablations sites will be apparent to those of ordinary skill in the art. Similarly, other anatomical structures that may be identified by stimulation with device 10) will be apparent to those of ordinary skill in the art.

In a sensing mode, rather than being used to deliver a signal to the heart, the device 10 is used to measure small signal electrograms at various points on the heart. These may be low frequency, low amplitude signals. To the extent that these signals may vary by location on the heart, it will be appreciated that a point contact may offer sufficient spatial resolution to discriminate between various signals. A sensing mode may therefore permit a user to identify the approximate location of particular anatomical structures or features based on sensed signals received through the device 10. Sensing (e.g., with device 10) may also be useful in assessing the performance of a conduction block (e.g., one created through ablation with device 10). For instance, prior to ablation, electrodes 122 may be placed on an area to be isolated through ablation, and the signal sensed at the area may be noted or recorded. After the area is isolated through ablation, the electrodes 122 may again be placed on the same area and compare the sensed signal reading to the one noted or recorded prior to ablation. By way of example only, where pulmonary veins 606, 608, 616, or 618 are conductively isolated through ablation, electrodes 122 may be placed on such pulmonary veins 606, 608, 616, or 618 after the ablation to see of electrical activity of the corresponding atrium 604 or 604 can be sensed. The success of the ablation may be judged by the degree to which the electrical activity of the atrium 604 or 604 can be sensed in the corresponding pulmonary veins 606, 608, 616, or 618. Other suitable targets for sensing, and ways in which sensing may be used, will be apparent to those of ordinary skill in the art.

In one example, the spacing between electrodes 122 on pacing tip 100 for use during sensing is approximately 2 mm. Of course, and other suitable spacing for electrodes 122 may be used. Similarly, any other suitable method for identifying the approximate location of particular anatomical structures or features may be used.

Where the device 10 is in communication with a power source (not shown) via the cord 18, the power source may comprise a user interface operable to receive user input indicating a particular task that the user intends to perform with the device 10. The power source may then communicate an appropriate signal to the electrodes 22, 122 in accordance therewith. Alternatively, the device 10 and/or power source may comprise a logic that is configured to detect the presence of a particular tip (e.g., the pacing tip 100) secured to the head 12 of the device 10, and may automatically vary the signal based on the detected tip. One exemplary power source that may be used with the device 10 is described in U.S. Provisional Patent Application Ser. No. 60/699,664, entitled "Matrix Router," filed Jul. 15, 2005, the disclosure of which is incorporated by reference herein. In yet another version, a user interface is provided on the device 10 for a user to select a particular mode of use. To the extent that a user interface is used, regardless of its location, the user interface may be operable to provide to the electrodes 22, 122 a signal having suitable parameters for a particular mode of use indicated by the user through the user input.

In another embodiment, the device 10 is configured such that the electrodes 22 may be used for both ablation and pacing, such as by merely changing the power output to the electrodes 22. It will therefore be appreciated that pacing and ablation may both be provided without the need to remove or secure a separate tip (e.g., the pacing tip 100 of FIGS. 5-7) from or to the head 12 of the device 10. Similarly, the electrodes 22 may be configured to permit use for all of ablation, pacing, stimulation, sensing, and any other tasks.

In yet another embodiment, the device 10 is varied such that the electrodes 122 of the pacing tip 100 are integral with the head 12. In one version of this embodiment, a separate ablation tip (not shown) is configured to selectively engage the pacing tip 100, such as by snapping onto the pacing tip 100 portion of the head 12. Such a separate ablation tip may also comprise a functional equivalent to the leaf spring portions 124 to provide electrical continuity between the pacing electrodes 122 and the ablation electrodes 22. In another version of this embodiment, the head 12 comprises two or more pairs of electrodes, each pair being dedicated to a particular task. For instance, a first pair of electrodes 22 may be dedicated to ablation, with a second pair of electrodes 122 being dedicated to pacing. In this version, the device 10 may be operable to electrically address a particular pair or set of electrodes (e.g., 22 or 122) in accordance with selections made by a user. By way of example only, such electrode selections may be made by a user via a user interface on the device 10 or a user interface on a separate control unit. Electrode selections may also be provided automatically based on a user's selection of a task to be performed via a user interface.

A few non-exhaustive examples of alternative tip designs are shown in FIGS. 10-13. Any of these alternative tip designs may be implemented integrally with the head 12, or may be provided in a removable tip (e.g., similar to pacing tip 100).

Figure 10:
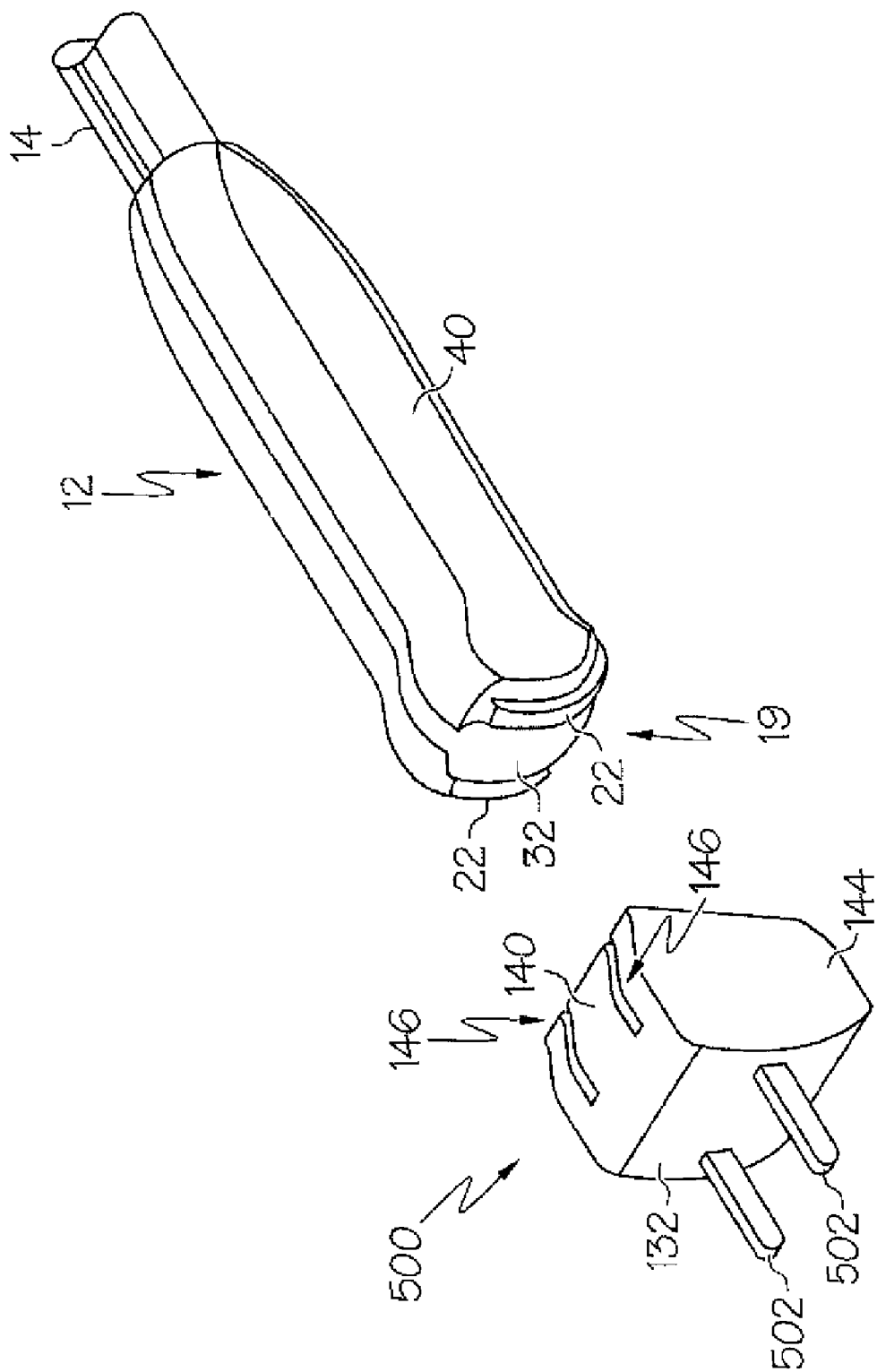
FIG. 10 illustrates a perspective view of an alternative head tip configured to engage the head of the ablation device of FIG. 1.

FIG. 10 shows a tip 500 having a pair of electrode prongs 502. In this embodiment, electrode prongs 502 are operable in a manner similar to electrodes 22 or 122 described above, with the difference being that electrode prongs 502 extend substantially from face 132 of tip 500. Thus, it will be appreciated that electrode prongs 502, or any suitable variation thereof, may be used to ablate, pace, sense, stimulate, or perform any other task. It will also be appreciated, particularly where electrode prongs 502 are substantially integral with head 12, that extension of electrode prongs 502 may be adjustable (e.g., via a lever, slider, or other input in handle 16). A user may therefore selectively adjust the amount of extension of electrode prongs 502 as desired.

Figure 11:
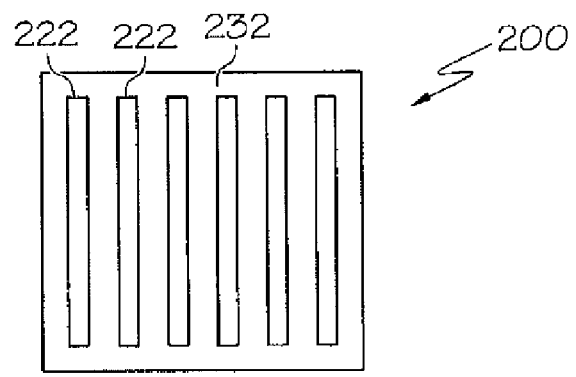
FIG. 11 illustrates a frontal view of an alternative head tip that may be used in addition to or in lieu of the head tips of FIG. 1-7 or 10.
Figure 12:
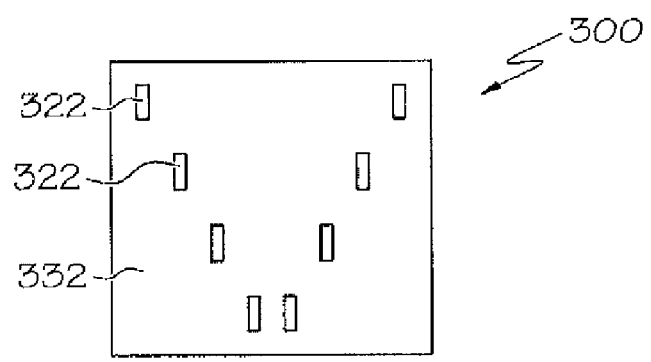
FIG. 12 illustrates a frontal view of an alternative head tip that may be used in addition to or in lieu of the head tips of FIG. 1-7 or 10-11.
Figure 13:
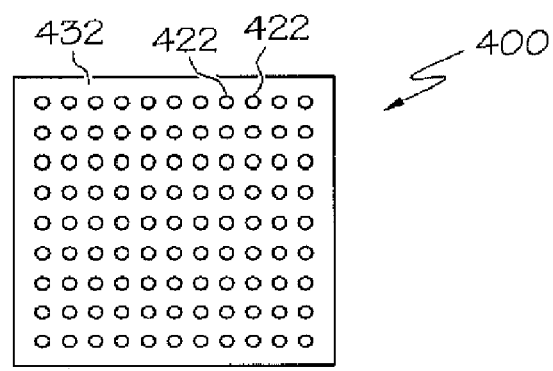
FIG. 13 illustrates a frontal view of an alternative head tip that may be used in addition to or in lieu of the head tips of FIG. 1-7 or 10-12.

FIG. 11 shows a tip 200 having a plurality of electrodes 222 disposed about a non-conductive face 232. FIG. 12 shows another tip 300 having a plurality of electrodes 322 disposed about a non-conductive face 332. FIG. 13 shows yet another tip 400 having a matrix or array of electrodes 422 disposed about a non-conductive face 432. It will be appreciated that each electrode 222, 322, 422 may extend from their respective face 232, 332, 432 to a degree similar to the extension of electrodes 122 from face 132 (e.g., generally co-planar with face 132 or a few millimeters from face 132). Alternatively, each electrode 222, 322, 422 may extend substantially from their respective face 232, 332, 432 in a manner similar to the extension of electrode prongs 502 from face 132 of tip 500. Other suitable degrees of extension will be apparent to those of ordinary skill in the art.

It will also be appreciated that, in the versions shown in FIGS. 11-13, each electrode 222, 322, 422 of a plurality may be individually electrically addressable (e.g., in accordance with user selections or automatic selections). It will also be appreciated that electrodes 222, 322, 422 may be addressable in pairs or sets. Suitable structures and techniques for addressing electrodes 222, 322, 422, as well as selections of electrodes 222, 322, 422 for being addressed in particular circumstances, will be apparent to those of ordinary skill in the art. In addition, it will be appreciated that any other suitable number or configuration of electrodes may be used.

Ablation Device with Sensors

Figure 14:
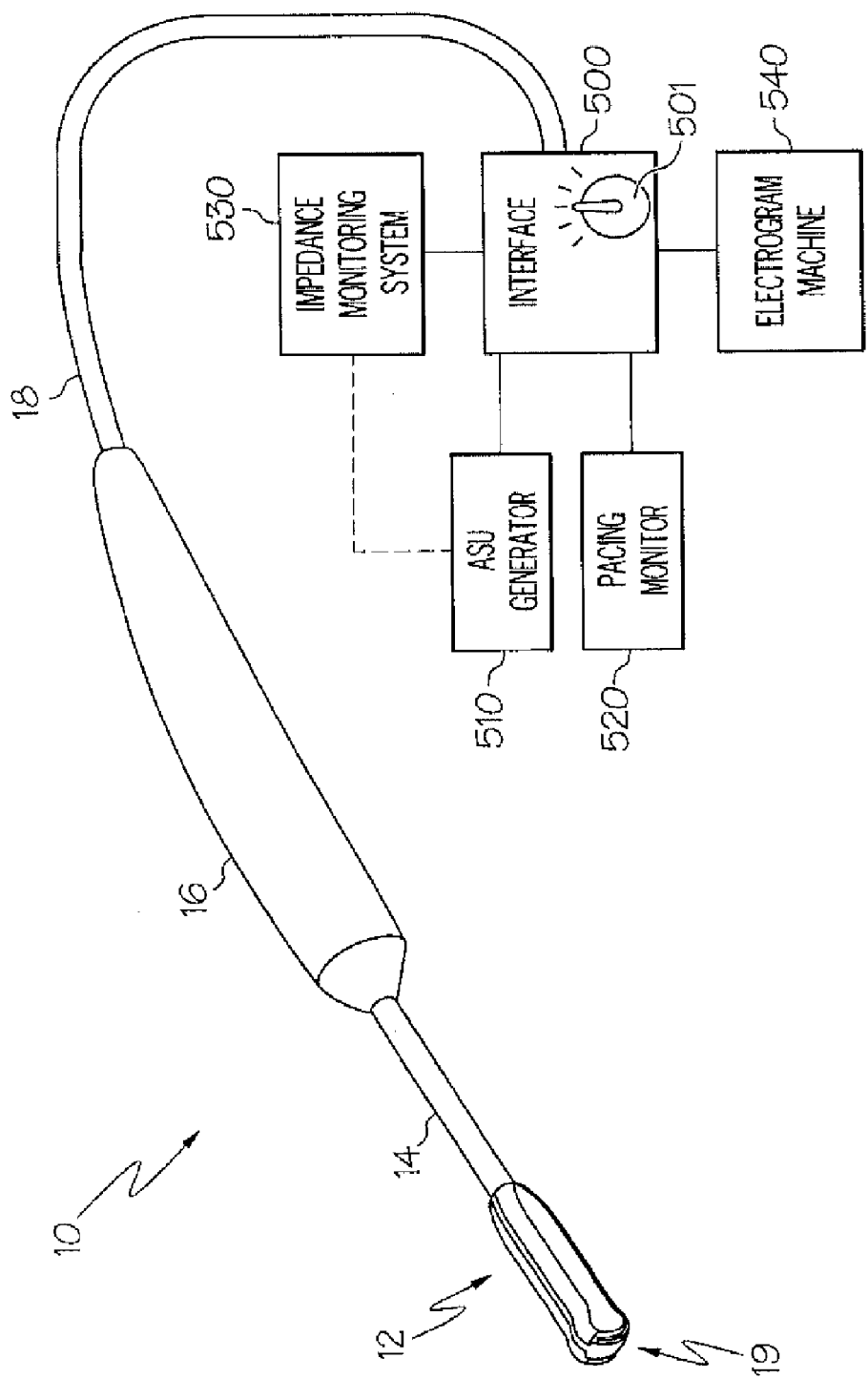
FIG. 14 illustrates an isometric view of the ablation device of FIG. 1 operably coupled to an interface and a plurality of devices such as sensors or a generator.

FIG. 14 illustrates an alternate example of an ablation device 10 described above. In addition to usage as ablation electrodes, the electrodes 22 of the ablation device 10 could be used in a number of other surgical application that could require two or more electrodes to contact tissue. During surgical procedures such as a cardiac MAZE procedure, a number of dual electrode probes or devices are used, and the probes can be connected to a variety of sensors or sensing devices to sense voltages, currents, continuity, and the like during the mapping of a heart, sensing tissue effects like impedance during coagulation, and sensing the effectiveness of a lesion placed in heart tissue. The sensing or energy delivery requirements can require different distances, spacing, energy levels and the like between the electrodes to produce a desired effect, or input to a sensor or sensing device.

In the above ablation device 10 design, there are two parallel electrodes 22 first pole electrode 23 and a second pole electrode 24, that are identical in size, and are spaced a distance apart on a distal tip of the above ablation device 10. Spacing between the electrodes 22 of ablation device 10 is selected for ablation effects such as lesion width and lesion depth. During ablation, an ASU generator 510 senses and measures tissue properties such as inductance across the electrodes 22 as tissue is coagulated, and can change electrical parameters such as power, current, and voltage until the tissue is transmural or "done".

Interconnector for Dual Electrode Sensors

FIG. 14 shows the ablation device 10 combined with an interconnector 500 that operably couples the ablation device 10 to a number of different common operating room equipment, devices or sensors that can include the ASU generator 510 to create lesions with electrodes 22, a pacing monitor 520 to provide electrical stimulus to tissue, an impedance monitoring system 530 for measuring tissue impedance and an electrogram machine 540 for measuring at least one of voltage, electrical conduction, conduction time, conduction velocity, and signal phase angle of the electrical signals that cause the heart to beat. Thus, interconnector 500 in combination with an electrosurgical device such as ablation device 10 can provide the surgeon with a single dual electrode device that could be used in lieu of a number of other dual electrode handheld devices commonly found in surgery. A switch 501 could be added to the interconnector 5000 to operably connect or disconnect one or more of the interconnected devices 510, 520, 530, 540 from the electrodes of a surgical device. Additionally, other electrical circuitry or components could be incorporated into the interconnector 500 such as diodes or switching circuitry. The circuitry 550 could protect interconnected sensing equipment from ablative energies or provide real time controls or switching circuitry. Thus, a surgeon could actuate the ASU generator 500 with a foot pedal and the circuitry 550 in the interconnector 500 would engage and protect sensitive pieces of equipment like the electrogram machine 540. For ablation device 10, each of the interconnected devices 510, 520, 530, 540 can be operably connected or disconnected to first pole electrode 23 and second pole electrode 24. If additional electrodes are present on a surgical device that can connect to interconnector 500, the interconnector 500 could accommodate the additional electrodes. The electrodes could be connected in any combination that could meet the needs of an energy delivery device or a sensing device, and this may be accomplished at the interconnector 500.

As described above, the spacing between the first pole electrode 23 and second pole electrode 24 can be different depending on whether the electrodes 23, 24 apply energy, or the electrodes are used for sensing. Special tips such as the pacing tip 100 described above can be configured to engage the head 12 of the device 10 and provide an electrode spacing that matches the needs of the selected interconnected device 510, 520, 530, or 540.

Variable Width Tip

In another alternate example, one of the electrodes 22, 23 can be made variable or adjustable relative to the other electrode to increase or decrease the electrode spacing to best match the needs of the selected interface coupled devices 510, 520, 530, 540.

Figure 15:
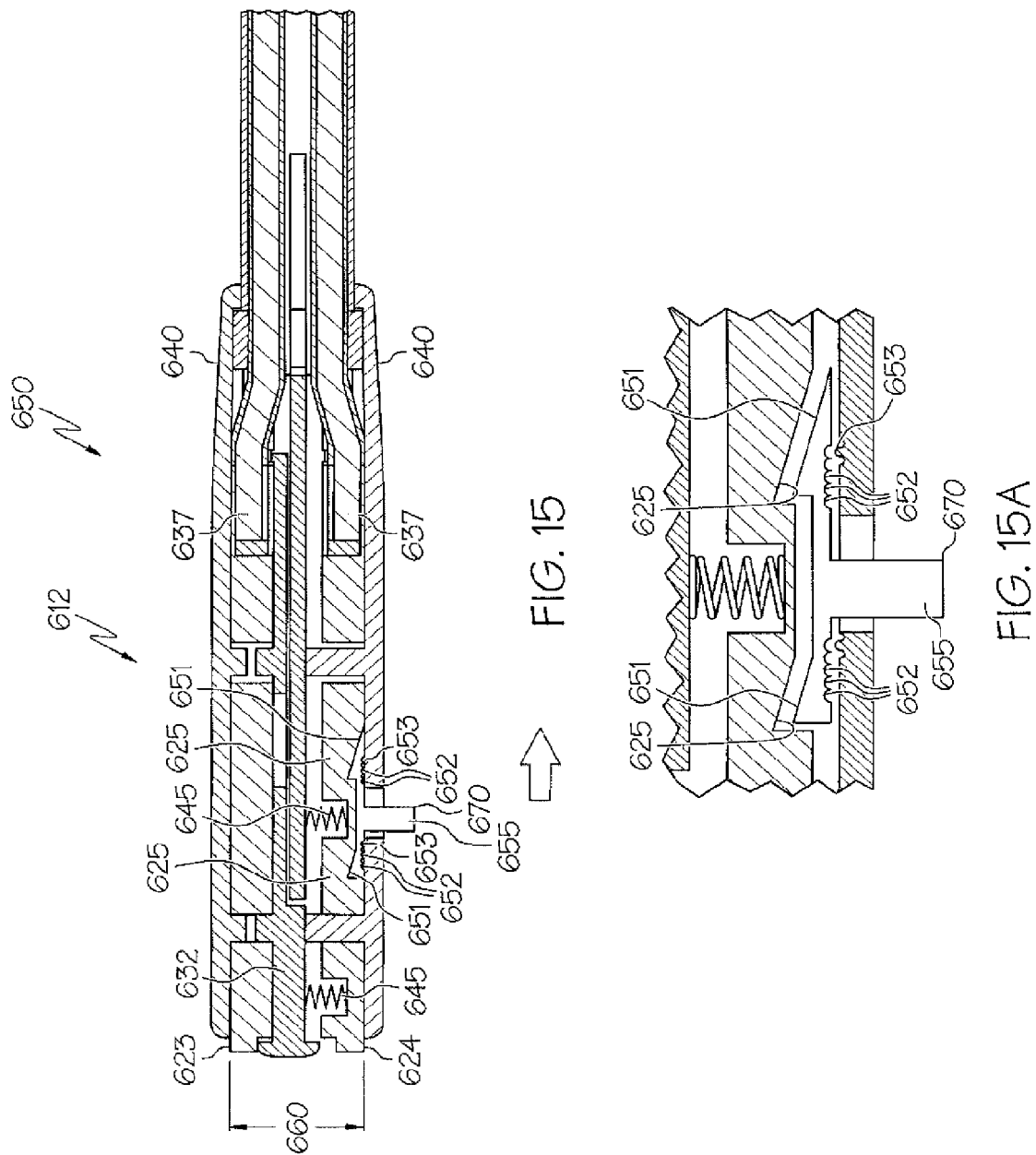
FIG. 15 illustrates the ablation device of FIG. 1 with a variable width electrode mechanism.

FIG. 15 shows an example of an electrode gap adjustment mechanism 650 that can be incorporated into a head 612 of an electrosurgical device 610. Electrode gap adjustment mechanism 650 is surrounded by a sheath 640 and has a fixed first pole electrode 623 and a moveable second pole electrode 624. An insulator 632 resides between first pole electrode 623 and second pole electrode 624. Moveable second pole electrode 624 is shown biased to a widest gap by springs 645. A slidable gap adjustor 670 has a pair of ramps 651 that engage with mating ramps 625 in second pole electrode 624. A plurality of detents 652 are located on slidable gap adjustor 670 and engage with detent features 653 in sheath 640. An actuator 655 extends through sheath 640 for the operator to adjust the gap 660 between electrodes 623, 624. Movement of the gap adjustor 650 in the direction of the arrow shown results in sliding contact between ramps 651 and mating ramps 652 and move electrode 624 towards electrode 623, compress springs 645, and narrow the gap 660. Detents 652, 653 hold the moveable electrode 624 at whatever gap setting 660 is selected. Widening of gap 660 when electrodes 623, 624 are in a narrowed position involves moving slidable gap adjustor 670 in the direction opposite to the arrow.

This description of a wedge type gap adjusting mechanism 650 is not meant to be limiting in any manner and other examples of gap adjustment mechanisms can include screws, linear and rotary cams, deflectable cantilevers, collars, and springs. Other suitable mechanisms for gap adjusting mechanisms, and ways in which gap adjusting mechanisms may be used, will be apparent to those of ordinary skill in the art.

Electrosurgical Device with Third Sensing Electrode

Figure 16:
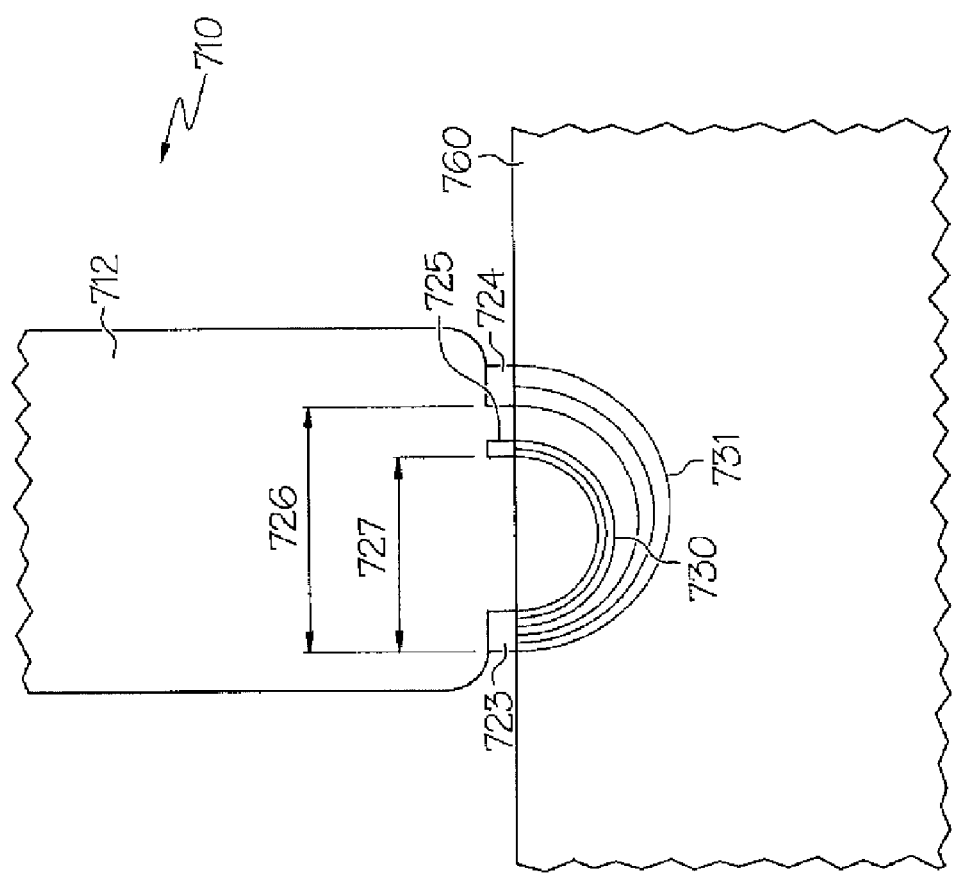
FIG. 16 illustrates a tip of the ablation device with a first pole electrode, a second pole electrode, and a third electrode and energy flowing therebetween.

FIG. 16 shows yet another example of an electrosurgical device with sensors. The electrosurgical device 710 has a head 712 having a first pole electrode 723, a second pole electrode 724 and a third electrode 725. As shown, third electrode 725 can be parallel to one or both of first pole electrode 723 and second pole electrode 724, and can be located between them. First pole electrode 723 and second pole electrode 724 can be spaced apart a first distance 726 that is conducive to ablation. Third electrode 725 can be used for sensing by being at a second distance 727 or sensing distance from one electrode such as first pole electrode 723 when first pole electrode 723 and third electrode 725 are connected to a sensor. Third electrode 725 could be much narrower in width than the first pole electrode 723 and the second pole electrode 724. Third electrode 725 could be electrically attached to second pole electrode 724 so that electrode 725 acts as another second polarity electrode during ablation. The electrodes 723, 724, 725 can also be used as sensors in any combination or ratio or combination of ratios to sense sensor measurements subut not limited to impedance, voltage, electrical conduction, conduction time, conduction velocity, and signal phase angle of the electrical signals.

When third electrode 725 is connected to second pole electrode 724 RF energy flows as follows. Lines 730 represents the flow of RF Bipolar energy from the first pole electrode 723 to the third electrode 725 and lines 731 represent flow from first pole electrode 723 to the second pole electrode 724 through tissue 760. As tissue 760 is cauterized, it becomes more of an insulator. As current flows from the first pole electrode 723 to the second pole electrode 724 and the third electrode 725, tissue 760 is cauterized to create a lesion along the flow of energy. When the lesion is sufficiently coagulated or transmural, the flow of energy to the third electrode 725 could be blocked while energy continues to flow between first pole electrode 723 and second pole electrode 724. As the ASU generator 510 is applying RF energy and sensing impedance, it could be sensing ablation progress by measuring impedance across the first pole electrode 723 to both the second pole electrode 723 and the smaller third pole electrode 725, or to the third pole electrode 725. Once the tissue towards the surface becomes ablated, energy will drive deeper into the tissue eventually flowing only between the two outer poles of electrodes 723, 724. Once this occurs, the third electrode 725 would be electrically isolated by cauterized tissue, sense no current flow, and therefore could be used as an indicator that the surface tissue was cauterized, and energy was being driven deep into tissue. This information could be an indicator for how deep the ablation has gotten.

Figure 17:
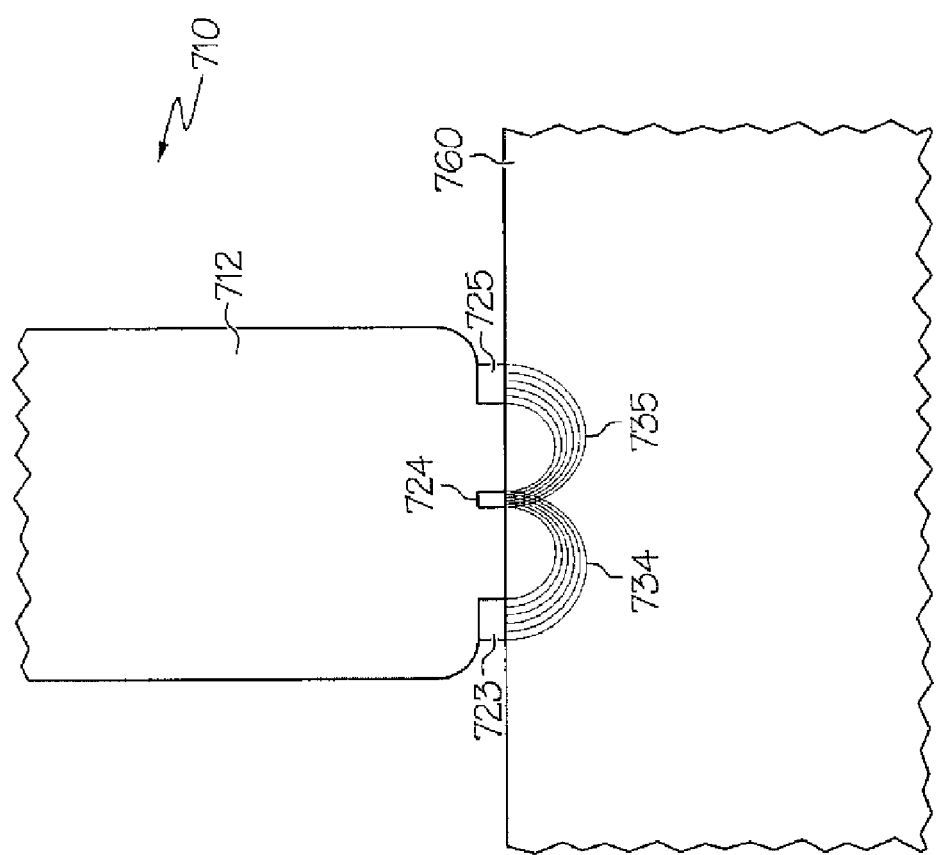
FIG. 17 illustrates a tip of the ablation device with a first pole electrode, a second pole electrode, and a central third electrode and energy flowing therebetween.

In another embodiment shown in FIG. 17 the three electrodes 723, 724, 725 may be equally spaced with third electrode 725 equidistant between first and second pole electrodes 723, 724 and energy. Use of a central third electrode 725 of a first polarity can communicate RF to outer electrodes 723 and 724 of a second polarity. Energy flow in tissue 760 is from central third electrode 725 to outer electrodes 723 and 724 as represented by lines 734, 735. This could allow more efficient ablation and triangulation of impedance. This electrode arrangement (as well as the one of FIG. 16) can offer various sensing arrangements that could enhance signal reception or cauterization accuracy. For example, with the three electrode arrangement, the sensing values can be taken across the center third electrode 725 and first pole electrode 723, as well as across the center third electrode 725 and second pole electrode 724. These sensor values could be ratioed to provide a side to side performance accuracy, and the ASU generator could alter energy flow to or from one of the outer electrodes 723, 724 to alter or correct lesion formation in tissue.

Alternately, the sensor values can be taken across the center third electrode 725 and first pole electrode 723, as well as across the center third electrode 725 and second pole electrode 724, and across the outer pair of electrodes 723, 724. By way of example, another sensor ratio can be created to improve performance accuracy by adding together the sensor values from the center third electrode 725 and first pole electrode 723, and across the center third electrode 725 and second pole electrode 724, and dividing the sum by the sensor value measured across the two outer electrodes. Any of the ratios above are merely exemplary, and any of the above the sensor information can be ratioed or combined in any manner to be used with any sensor devices such as the interface coupled devices 510, 520, 530, 540.

Figure 18:
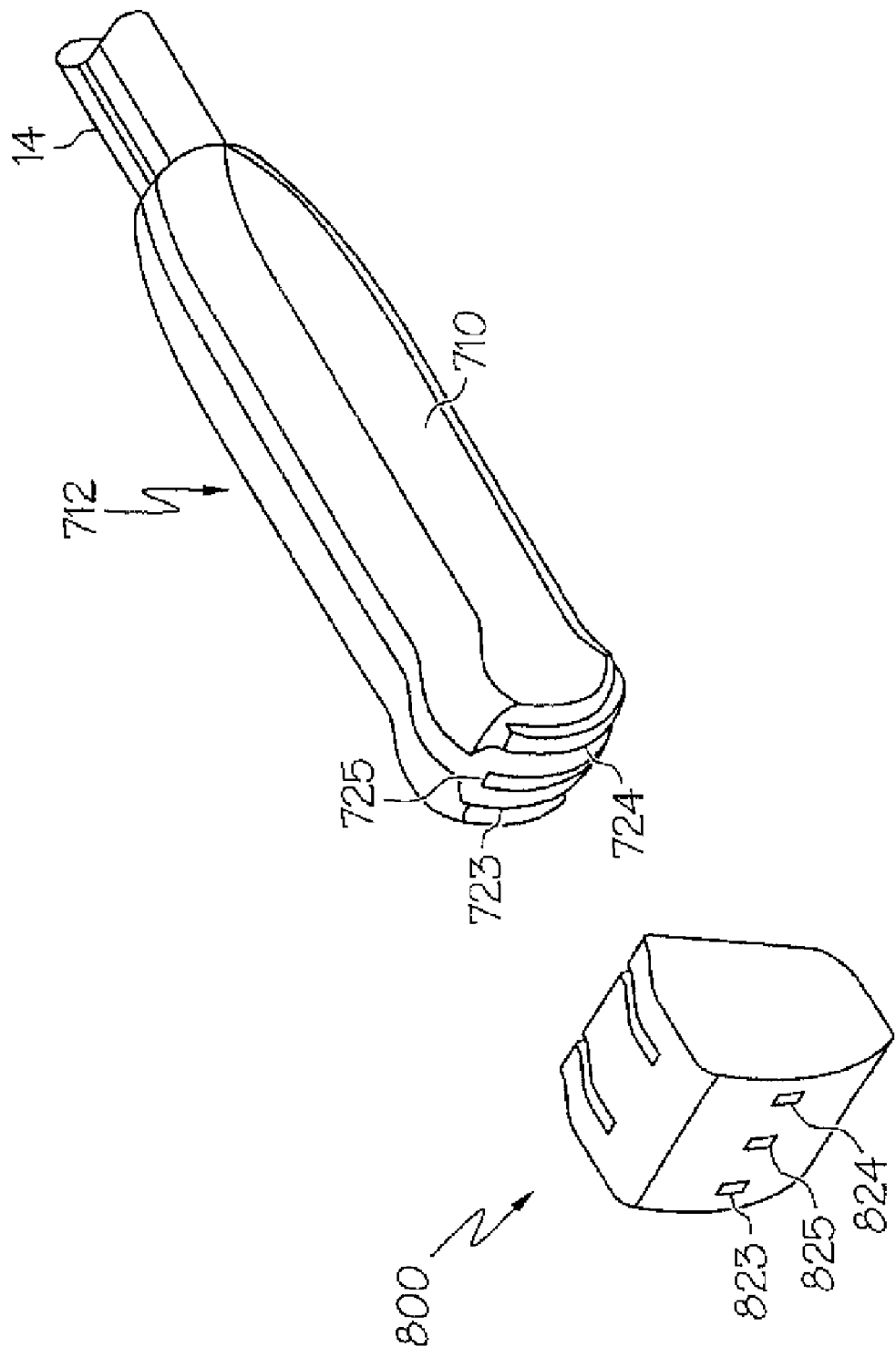
FIG. 18 illustrates a frontal view of an alternative head tip that may be used with a head of FIG. 15 or FIG. 16.

Additionally, by way of example, any cap type devices described above such as cap 200 can incorporate a third electrode to be used with the 3 electrode head 712. One example of a three electrode cap 800 is shown in FIG. 18 with electrodes 823, 824, 825. Any electrode configuration or spacing described above for a cap could be included.

Method of Use of an Ablation Device with Sensors

The MAZE or MINI MAZE surgical procedure using an electrosurgical device such as electrosurgical device 612 begins with a voltage mapping procedure that connects tissue contact electrodes 623, 624 to a sensor such as echogram machine 540 to map the location of natural electrical signals that stimulate the heartbeat. Once the location of the impulses are found and mapped, the surgeon uses the interconnector 500 to select a pacing monitor 540 to be connected to the electrodes 623, 624. The electrodes 623, 624 are adjusted to a pacing gap with a gap adjusting mechanism 650 and are placed into contact with tissue at a number of the mapped positions. At each position the electrodes 623, 624 are energized to stimulate the heart or heartbeat. If no response occurs, the voltage is increased, and the stimulation is re-supplied until the heart reacts. This determines the stimulation threshold voltage at each site. The stimulation locations, stimulation responses, and threshold voltages are noted on the heart map and are used to identify the location of the specific nerves that are responsible for the irregular heartbeat. Once the heart has been mapped, the electrosurgical device 612 is removed from the patient and the electrodes 623, 624 are adjusted to an electrode gap conducive to the application of RF energy to the heart to create lesions therein. RF energy is applied via the electrodes 623, 624 to create one or more coagulated lesions on the heart. The electrodes 623, 624 can also be used to monitor tissue effects such as impedance during ablation. After the lesions of cauterized tissue are placed onto the heart, the electrosurgical device 612 is again removed. The efficacy of the lesion is sensed by adjusting the electrodes 623, 624 to a sensing gap, connecting them to echogram machine 540 via interconnector 500 and placing them across the lesion. If there is no continuity across the lesion, the lesion was successful. Alternately, or in addition to the echogram machine 540, the electrodes 623, 624 can be connected to a pacing monitor 520 to apply stimulation voltages as an alternate check of the efficacy of the lesion. If the stimulation voltages fail to stimulate across the lesions, the lesion was successful.

Thus, sensing can be accomplished with a single pair of electrodes applied to tissue during mapping, during ablation, and during efficacy checks of the lesion. Alternately, a third sensing electrode can be used.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

While preferred embodiments of the present invention have been shown and described herein, it will be obvious to those skilled in the art, given the benefit of the present disclosure, that such embodiments are provided by way of example only. Numerous variations, changes, and substitutions will now occur to those skilled in the art without departing from the spirit and scope of the appended claims.

What is claimed is:

1. An electro surgical device comprising:
   a first rail electrode having a convex profile that extends distally away from, and is mounted to, a distal insulated housing, the first rail electrode having a length to width ratio greater than or equal to 4:1;
   a second rail electrode having a convex profile that extends distally away from, and is mounted to, the distal insulated housing, the second rail electrode having a length to width ratio greater than or equal to 4:1, the second rail electrode oriented in parallel to be first rail electrode; and,
   an electrode gap adjuster at least partially located within the housing and mounted to the housing, the electrode gap adjuster mounted to at least one of the first rail electrode and the second rail electrode and configured to adjust a widthwise spacing between the first rail electrode and the second rail electrode.

2. The electrosurgical device of claim 1, wherein the electrode gap adjuster is configured to maintain parallelism between the first rail electrode and the second rail electrode at different widthwise spacings.

3. The electrosurgical device of claim 1, wherein the electrode gap adjuster includes at least one of a screw, a ramp, a cam, a cantilever, and a spring.

4. The electrosurgical device of claim 1, further comprising a third rail electrode having a convex profile that extends distally away from the distal housing, the third rail electrode oriented in parallel to the first rail electrode and the second rail electrode, wherein the electrode gap adjuster is configured to adjust a widthwise spacing between at least one of (a) the first rail electrode and the third rail electrode, and (b) the second rail electrode and the third rail electrode.

5. The electrosurgical device of claim 1, wherein to the widthwise spacing is optimized for at least one of voltage measurement, impedance measurement, conduction measurement, conduction velocity measurement, conduction phase angle measurement, lesion width, lesion depth, stimulation energy delivery, and RF energy delivery.

6. The electro surgical device of claim 1, wherein the electrode gap adjuster is interposed between the first rail electrode and the second rail electrode.

7. The electro surgical device of claim 1, further comprising a cap removably coupled to the distal insulated housing, wherein the cap includes a first cap electrode distally extending from the cap and in electrical communication with the first rail electrode via a first electrical connection, wherein the cap includes a second cap electrode distally extending from the cap and in electrical communication with the second rail electrode via a second electrical connection, and wherein the first cap electrode and the second cap electrode have a widthwise spacing that is different from a widthwise spacing between the first rail electrode and the second rail electrode.

8. An electro surgical device comprising:
a distal insulated housing including a first rail electrode and a second rail electrode mounted to and exposed with respect to, the insulated housing, both the first and second rail electrodes include a length to width ratio greater than or equal to 4:1 and a widthwise gap that extends along the length of the first and second electrodes;
a tip removably mounted to a distal end of the insulated housing, the tip including a first tip electrode and a second tip electrode distally extending from a distal end of the tip, wherein the first tip electrode is configured to be in electrical communication with the first rail electrode when the tip is mounted to the distal end of the insulated housing, wherein the second tip electrode is configured to be in electrical communication with the second rail electrode when the tip is mounted to the distal end of the insulated housing, and wherein at least one of a shape and a widthwise gap associated with the first and second tip electrodes is different than at least one of a shape and the widthwise gap associated with the first and second rail electrodes.

9. The electro surgical device of claim 8, wherein:
the first and second tip electrodes includes a length to width ratio greater than or equal to 4:1; and,
the widthwise gap of the first and second tip electrodes is less than the widthwise gap of the first and second rail electrodes.

10. The electro surgical device of claim 8, wherein:
the first and second tip electrodes include a length to width ratio greater than or equal to 4:1; and,
the widthwise gap of the first an second tip electrodes is greater than the widthwise gap of the first and second rail electrodes.

11. The electrosurgical device of claim 8, further comprising:
a third rail electrode mounted to, and exposed with respect to, the insulated housing; and,
a third tip electrode distally extending from the distal end of the tip, wherein the third tip electrode is configured to be in electrical communication with the third rail electrode when the tip is mounted to the distal end of the insulated housing.

12. The electrosurgical device of claim 11, wherein:
at least one of a shape and a widthwise gap associated with the first and third tip electrodes is different than at least one of a shape and a widthwise gap associated with the first and third rail electrodes; and,
at least one of a shape and a widthwise gap associated with the second and third tip electrodes is different at least one shape and a widthwise gap associated with the second and third rail electrodes.

13. The electrosurgical device of claim 8, wherein at least one of a shape and a widthwise gap associated with the first and second tip electrodes is optimized for at least one of voltage measurement, impedance measurement, conduction measurement, conduction velocity measurement, conduction phase angle measurement, lesion width, lesion depth, stimulation energy delivery, and RF energy delivery.

* * * * *